US012583829B2

(12) United States Patent
Li et al.

(10) Patent No.: US 12,583,829 B2
(45) Date of Patent: Mar. 24, 2026

(54) SALT OF BENZOTHIAZOLE COMPOUND, AND CRYSTAL FORM AND USE THEREOF

(71) Applicant: Sichuan Kelun Pharmaceutical Research Institute Co., Ltd., Sichuan (CN)

(72) Inventors: Long Li, Sichuan (CN); Shidong Yi, Sichuan (CN); Tianming Wang, Sichuan (CN); Pingyun Chen, Sichuan (CN); Chengxi Yang, Sichuan (CN); Jingyi Wang, Sichuan (CN)

(73) Assignee: Sichuan Kelun Pharmaceutical Research Institute Co., Ltd., Chengdu Sichuan (CN)

( * ) Notice: Subject to any disclaimer, the term of this patent is extended or adjusted under 35 U.S.C. 154(b) by 397 days.

(21) Appl. No.: 18/027,246

(22) PCT Filed: Nov. 9, 2021

(86) PCT No.: PCT/CN2021/129537

§ 371 (c)(1),
(2) Date: Mar. 20, 2023

(87) PCT Pub. No.: WO2022/105644

PCT Pub. Date: May 27, 2022

(65) Prior Publication Data

US 2023/0365518 A1 Nov. 16, 2023

(30) Foreign Application Priority Data

Nov. 19, 2020 (CN) ......................... 202011304450.1

(51) Int. Cl.
*C07D 277/82* (2006.01)
*A61K 31/428* (2006.01)

(52) U.S. Cl.
CPC ........ *C07D 277/82* (2013.01); *C07B 2200/13* (2013.01)

(58) Field of Classification Search
CPC ..... C97D 277/82; A61K 31/428; A61P 25/16; C07D 277/82
USPC .......................................... 548/161; 514/367
See application file for complete search history.

(56) References Cited

U.S. PATENT DOCUMENTS 4,731,374 A 3/1988 Griss et al.
2014/0377365 A1 12/2014 Wu et al.

FOREIGN PATENT DOCUMENTS

| | | | |
|---|---|---|---|
| CN | 102784111 | A | 11/2012 |
| CN | 111212640 | A | 5/2020 |
| CN | 113730349 | A | 12/2021 |
| WO | 2008000418 | A2 | 1/2008 |
| WO | 2019036624 | A1 | 2/2019 |

OTHER PUBLICATIONS

International Search Report issued Feb. 11, 2022 in PCT/CN2021/129537.
Written Opinion issued Feb. 11, 2022 in PCT/CN2021/129537.
Partial Supplemental European Search Report issued Nov. 18, 2024.

*Primary Examiner* — Charanjit Aulakh
(74) *Attorney, Agent, or Firm* — Ice Miller LLP

(57) ABSTRACT

Provided in the present invention are a salt of a benzothiazole compound as represented by formula I and a crystal form and the use thereof. The salt is selected from pamoate and palmitate. Further provided is the use of the salt of the compound of formula I and the crystal form thereof in the preparation of a drug for treating Parkinson's disease and restless leg syndrome.

I

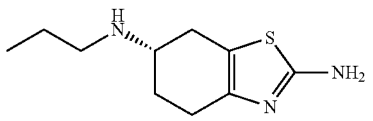

28 Claims, 8 Drawing Sheets

SALT OF BENZOTHIAZOLE COMPOUND, AND CRYSTAL FORM AND USE THEREOF

CROSS-REFERENCE TO RELATED APPLICATION

This application is a Section 371 of International Application No. PCT/CN2021/129537 filed Nov. 9, 2021, which was published in the Chinese language May 27, 2022, under International Publication No. WO 2022/105644 A1, which claims priority to Chinese Patent Application No. 202011304450.1 filed Nov. 19, 2020, the disclosures of which are incorporated herein by reference in their entireties.

TECHNICAL FIELD

The present disclosure relates to a salt of (S)-2-amino-4,5,6,7-tetrahydro-6-propylamine-benzothiazole and crystal form and use thereof.

BACKGROUND

Parkinson's disease (PD) is a motor system disorder of nervous system. PD is characterized as progressive disease, which affects movement and leads to the loss of brain cells that produce dopamine, causing tremor of hands, arms, legs, jaw and face, and/or rigidity or stiffness of limbs and trunk. The main symptoms include muscle rigidity, slow movement, static tremor and postural instability.

(S)-2-amino-4,5,6,7-tetrahydro-6-propylamine-benzothiazole (hereinafter referred as "compound of formula I") is a non-ergot dopamine receptor agonist developed by Boehringer Ingelheim, Germany. At present, the main products on the market domestic and abroad are quick release hydrochloride tablets and sustained release hydrochloride tablets, which are used to treat Parkinson's disease and restless leg syndrome.

According to the survey, most of Parkinson's patients are middle-aged and elderly people, and the incidence of dysphagia is as high as 70-90%, which increases the risk of aspiration pneumonia by 15-50%. The dysphagia occurs in the early stage of the disease and is along with the whole course of the disease, which is extremely easy to cause cough, which increases the risk of aspiration pneumonia, and aspiration pneumonia is one of the main causes of death of Parkinson's patients. At present, the clinical drugs are mainly taken orally, and they need to be administered many times a day. The single dose is large, and the compliance needs to be improved urgently. In addition, the pulse like stimulation secondary to the fluctuation of dopamine blood concentration will further aggravate the level and dysfunction of dopaminergic receptor. Only continuous and stable dopamine stimulation can control or reduce the occurrence of adverse effects of exercise complications. In addition, a long-acting release protocol of more than 24 hours will also help patients to comply, because patients with advanced PD usually do not comply, making it difficult to assess whether patients have received the appropriate dose of drugs.

In view of above, the clinical practice recommends the use of long-acting sustained release formulations, such as oral slow and controlled release agent, long-acting patch, and long-acting injection, to maintain a stable blood drug concentration and improve patient compliance. Therefore, it is desirable to develop salt forms and crystal forms that can be used for long-acting sustained release formulations.

SUMMARY

In first aspect, provided is a salt of (S)-2-amino-4,5,6,7-tetrahydro-6-propylamine-benzothiazole (the structural formula is shown as formula I), wherein the salt is selected from the group consisting of pamoate and palmitate,

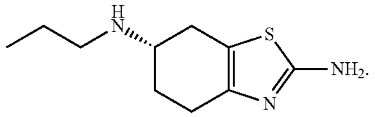

I

In some embodiments, the salt of the compound of formula I is a palmitate.

In second aspect, provided are crystal forms of salts of the compound of formula I, for example crystal forms A-S of the pamoate and crystal forms T-V of the palmitate of the compound of formula I.

In third aspect, provided is a pharmaceutical composition comprising a salt of the compound of formula I, which is selected from the group consisting of pamoate and palmitate, and particularly crystal forms of the pamoate or crystal forms of the palmitate of the compound of formula I, and one or more pharmaceutically acceptable carriers.

In fourth aspect, provided is use of the salt or crystal form of the compound of formula I, especially the crystal forms A-S of the pamoate and crystal forms T-V of the palmitate of the compound of formula I or a pharmaceutical composition, in the manufacture of a medicament for the treatment of Parkinson's disease and restless leg syndrome.

The salts or crystal forms of the compound of formula I of present disclosure have a low solubility, which can achieve the sustained release effect and prepare a long-acting sustained-release formulation.

DETAILED DESCRIPTION OF THE DISCLOSURE

Definitions

Figure 1:
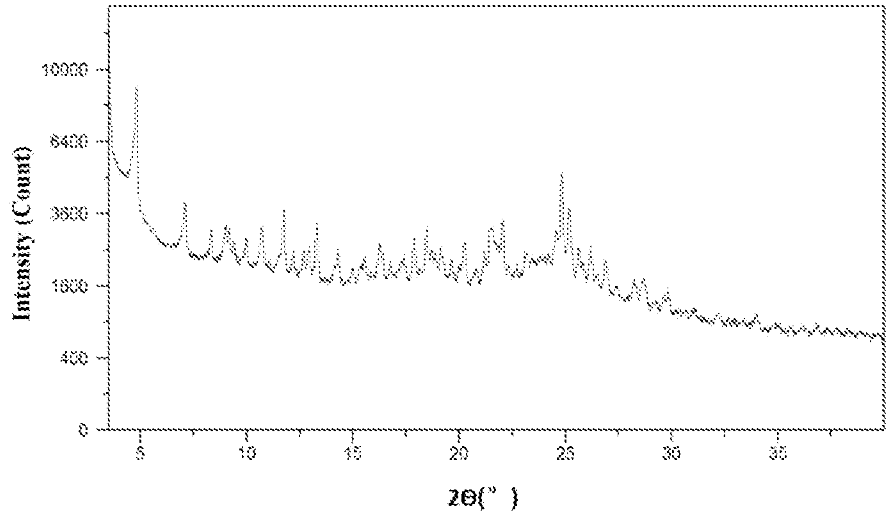
FIG. 1 shows the X-ray powder diffraction (XRPD) pattern of crystal form A of the pamoate of the compound of formula I.

Unless otherwise defined below, the meanings and intentions of all technical terms and scientific terms used herein are the same with those commonly understood by those skilled in the art. Reference to the technologies used herein intends to refer to the technologies as commonly understood in the art, including those changes in technologies or replacement of equivalent technologies that are obvious to those skilled in the art. Although it is believed that the following terms are well understood by those skilled in the art, the following definitions are still described to better explain present disclosure.

As used herein, the term "include", "comprise", "have", "contain" or "relate to" and other variants used herein are meant to be inclusive or open-ended, which does not exclude other unlisted elements or method steps.

As used herein, the word "about" refers to the acceptable standard error of the said value considered by those of ordinary skill in the art, such as ±0.05, ±0.1, ±0.2, ±0.3, ±1, ±2 or ±3.

The terms "compound I" and "compound of formula I" used herein refer to compounds with the following formula I, which can be used interchangeably herein.

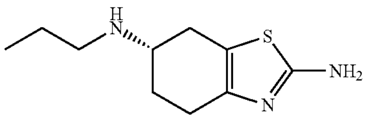

I

The term "pharmaceutical composition" refers to an active ingredient, which can optionally be combined with one or more pharmaceutically acceptable chemical ingredients (for example, but not limited to carriers and/or excipients). The active ingredient is for example compound of formula I or its pamoate or palmitate, one or more of the crystal forms of present disclosure or one or more of the crystalline compositions of present disclosure.

The terms "administration" or "administering" and the like refer to methods by which a compound or composition can be delivered to the desired site of biological action. These methods include but not limited to oral, parenteral (including intravenous, subcutaneous, intraperitoneal, intramuscular, intravascular injection or infusion), topical, rectal administration, and the like.

For drugs or pharmacologically active agents, the term "effective amount" refers to a non-toxic but adequate amount of drugs or agents that can achieve the desired effect. For the oral dosage form of present disclosure, the "effective amount" of one active substance in the composition can be an amount needed to achieve the desired effect when used in combination with another active substance in the composition. The effective amount may be determined individually and depends on the age and general condition of the receptor as well as specific active substance. The effective amount in specific case can be determined by a person skilled in the art through conventional test.

The terms "active ingredient", "therapeutic agent", "active substance" or "active agent" refer to a chemical entity that can effectively treat or prevent the target disorder, disease, or symptom. The term herein can refer to, for example, the compound of formula I or a pamoate or a palmitate, thereof, one or more of the crystal forms of present disclosure or one or more of the crystalline compositions of present disclosure.

The term "amorphous" used herein refers to any solid substance which lacks order in three dimensions. In some cases, amorphous solids can be characterized by known techniques, including XRPD crystallography, solid-state nuclear magnetic resonance (ssNMR) spectroscopy, DSC, or some combination of these techniques. As explained below, amorphous solids produce dispersive XRPD pattern, which usually includes one or two broad peaks (i.e., with about 5° 2 θ or a larger base width peak).

The term "crystal form" or "crystal" used herein refers to any solid substance exhibiting a three-dimensional order, as opposed to amorphous solid substance, which produces a characteristic XRPD pattern with peaks having clear boundaries.

As used herein, the term "X-ray powder diffraction pattern (XRPD pattern)" refers to the experimentally observed diffraction pattern or the parameters derived from it. XRPD patterns are typically characterized by peak position (abscissa) and/or peak intensity (ordinate).

In an X-ray powder diffraction (XRPD or XRD) spectrum, the diffraction patterns obtained from crystalline compounds are often characteristic for specific crystal forms, in which the relative intensity of the spectral bands (especially at low angles) may change due to the dominant orientation effect caused by differences in crystallization conditions, particle sizes and other measurement conditions. Therefore, the relative intensity of the diffraction peak is not characteristic of the targeted crystal form. When judging whether it is the same with the known crystal form, more attention should be paid to the relative position of the peak rather than their relative intensity. In addition, for any given crystal form, the position of the peak may have a slight error, which is also known in the field of crystallography. For example, due to the temperature change, sample movement or instrument calibration during sample analysis, the peak position can be moved, the measurement error of the 2θ value is sometimes about ±0.2°. Therefore, this error should be taken into account when determining each crystal form structure. If the crystal form of present disclosure is described as substantially as shown in the designated drawings, the term "substantially" is also intended to cover such differences in diffraction peak positions.

The 2θ angle or interplanar spacing d is usually used in XRPD pattern to represent the peak position, and there is a simple conversion relationship between them: d=λ/2 sin θ, wherein d represents the interplanar spacing, λ represents wavelength of incident X-ray, θ is the diffraction angle. For the same crystal form of the same compound, the XRPD peak positions are similar on the whole, and the relative intensity error may be large. It should also be pointed out that in the identification of the mixture, some of the diffracted rays will be lost due to factors such as the decrease of the content. At this time, it is unnecessary to rely on all the spectral bands observed in the high-purity sample, and even one spectral band may be characteristic for a given crystal.

As used herein, the term "2θ" refers to the peak position in degrees set by the experiment based on the X-ray diffraction experiment, and is usually the abscissa unit in the diffraction pattern. If the reflection is diffracted when the incident beam forms an angle θ with a lattice plane, the experimental setup requires recording the reflected beam at an angle of 2θ. It should be understood that references herein to specific 2θ values for a specific crystal form are intended to represent 2θ values (in degrees) measured using the X-ray diffraction experimental conditions described herein.

As used herein, the term "thermogravimetric analysis (TGA) pattern" refers to the curve recorded by the thermogravimetric analyzer.

As used herein, the term "differential scanning calorimetry (DSC) pattern" refers to the curve recorded by the differential scanning calorimeter.

As used herein, the term "nuclear magnetic resonance ($^1$H-NMR) pattern" refers to the signal peak recorded by the nuclear magnetic resonance instrument.

As used herein, the term "substantially the same" with respect to an X diffraction peak position means to take into account representative peak positions and intensity variations. For example, those skilled in the art will understand the peak position (2θ) will display some changes, usually up to 0.1-0.2 degrees, and the instrument used to measure diffraction will also display some changes. In addition, those skilled in the art will understand that the relative peak intensity will show changes between instruments and changes due to the degree of crystallinity, preferred orientation, prepared sample surface and other factors known to those skilled in the art, and should be regarded as a qualitative measurement only.

As used herein, the term "room temperature" refers to 20° C.±5 Ge.

Salt and Crystal Form of the Compound of Formula I

Provided is a salt of (S)-2-amino-4,5,6,7-tetrahydro-6-propylamine-benzothiazole (Compound of formula I), wherein the salt is selected from the group consisting of pamoate and palmitate,

I

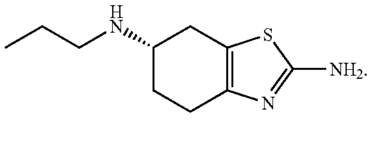

In other embodiments, the salt of the compound of formula I is a palmitate of the compound of formula I.

In some embodiments, the salt of the compound of formula I is a pamoate of the compound of formula I.

Pamoate of the Compound of Formula I and Crystal Form Thereof (1:1)

In some embodiments, the stoichiometric ratio of the compound of formula I to pamoic acid in the pamoate of the compound of formula I is 1:1.

Crystal Form A

In some embodiments, provided is a crystal form A of the pamoate of the compound of formula I, wherein the stoichiometric ratio of the compound of formula I to pamoic acid is 1:1, and the crystal form A of the pamoate of the compound of formula I has an XRPD pattern comprising 2θ diffraction peak at about 4.76±0.2°, 7.07±0.2°, 8.32±0.2°, 10.7±0.2°, 11.73±0.2°, 13.29±0.2°, 16.25±0.2°, 18.45±0.2°, 21.51±0.2°, 24.81±0.2° and 26.17±0.2°. Preferably, the crystal form A of the pamoate of the compound of formula I has an XRPD pattern further comprising 2θ diffraction peak at about 17.87±0.2°, 22.01±0.2°, 25.17±0.2°.

In some embodiments, the crystal form A of the pamoate of the compound of formula I has an XRPD pattern comprising 2θ diffraction peak at about 4.76±0.2°, 7.07±0.2°, 8.32±0.2°, 10.7±0.2°, 11.73±0.2°, 13.29±0.2°, 16.25±0.2°, 17.87±0.2°, 18.45±0.2°, 21.51±0.2°, 22.01±0.2°, 24.81±0.2°, 25.17±0.2° and 26.17±0.2°.

In some embodiments, the crystal form A of the pamoate of the compound of formula I has an XRPD pattern comprising the following 2θ diffraction peak at:

| 2θ (°) ± 0.2° | intensity % |
|---|---|
| 4.76 | 100 |
| 7.07 | 36.26 |
| 8.32 | 19.16 |
| 8.99 | 22.47 |
| 9.17 | 18.79 |
| 9.39 | 13.46 |
| 9.96 | 16.5 |
| 10.7 | 28.43 |
| 11.05 | 5.50 |
| 11.73 | 42.62 |
| 12.17 | 11.42 |
| 12.68 | 15.05 |
| 12.91 | 17.42 |
| 13.29 | 34.21 |
| 14.25 | 15.85 |
| 14.95 | 7.49 |
| 15.48 | 12.07 |
| 16.25 | 21.60 |
| 16.41 | 12.08 |
| 16.74 | 10.79 |
| 17.32 | 11.47 |
| 17.87 | 25.74 |
| 18.45 | 33.05 |
| 18.69 | 17.24 |
| 19.13 | 17.14 |
| 19.64 | 12.37 |
| 20.23 | 25.98 |
| 20.76 | 8.22 |
| 21.17 | 12.59 |
| 21.51 | 41.57 |
| 22.01 | 35.79 |
| 23.45 | 8.29 |
| 24.56 | 24.26 |
| 24.81 | 84.08 |
| 25.17 | 43.31 |
| 25.61 | 18.72 |
| 25.81 | 11.58 |
| 26.17 | 25.73 |
| 26.46 | 6.62 |
| 26.88 | 17.87 |
| 27.37 | 5.07 |
| 28.23 | 10.73 |
| 28.65 | 13.31 |
| 29.22 | 2.76 |
| 29.62 | 8.06 |

-continued

| 2θ (°) ± 0.2° | intensity % |
|---|---|
| 29.81 | 12.33 |
| 31.03 | 2.93 |
| 32.41 | 2.05 |
| 33.95 | 5.98 |
| 34.89 | 2.63 |
| 35.57 | 3.76 |
| 36.11 | 2.85 |
| 36.80 | 3.25 |
| 38.31 | 2.08 |

In some embodiments, the crystal form A of the pamoate of the compound of formula I has an XRPD pattern substantially as shown in FIG. 1. In some preferred embodiments, the crystal form A of the pamoate of the compound of formula I has an XRPD pattern as shown in FIG. 1.

Crystal Form B

In some embodiments, provided is a crystal form B of the pamoate of the compound of formula I, wherein the stoichiometric ratio of the compound of formula I to pamoic acid is 1:1, and the crystal form B of the pamoate of the compound of formula I has an XRPD pattern comprising 2θ diffraction peak at about 5.79±0.2°, 6.38±0.2°, 10.95±0.2°, 14.72±0.2°, 17.61±0.2°, 18.40±0.2°, 19.81±0.2° and 22.18±0.2°. Preferably, the crystal form B of the pamoate of the compound of formula I has an XRPD pattern further comprising 2θ diffraction peak at about 10.61±0.2°, 12.51±0.2°, 17.61±0.2° and 20.01±0.2°. More preferably, the crystal form B of the pamoate of the compound of formula I has an XRPD pattern further comprising 2θ diffraction peak at about 10.18±0.2°, 13.15±0.2° and 13.36±0.2°.

In some embodiments, the crystal form B of the pamoate of the compound of formula I has an XRPD pattern comprising 2θ diffraction peak at about 5.79±0.2°, 6.38±0.2°, 10.61±0.2°, 10.95±0.2°, 12.51±0.2°, 14.72±0.2°, 17.61±0.2°, 18.40±0.2°, 19.81±0.2°, 20.01±0.2° and 22.18±0.2°. In other embodiments, the crystal form B of the pamoate of the compound of formula I has an XRPD pattern comprising 2θ diffraction peak at about 5.79±0.2°, 6.38±0.2°, 10.18±0.2°, 10.61±0.2°, 10.95±0.2°, 12.51±0.2°, 13.15±0.2°, 13.36±0.2°, 14.72±0.2°, 17.61±0.2°, 18.40±0.2°, 19.81±0.2°, 20.01±0.2° and 22.18±0.2°.

In some embodiments, the crystal form B of the pamoate of the compound of formula I has an XRPD pattern comp rising the following 2θ diffraction peak at:

| 2θ (°) ± 0.2° | intensity % |
|---|---|
| 5.79 | 64.48 |
| 6.38 | 19.62 |
| 8.79 | 11.03 |
| 9.38 | 13.35 |
| 10.18 | 31.69 |
| 10.61 | 100 |
| 10.95 | 44.15 |
| 11.20 | 17.63 |
| 12.51 | 31.33 |
| 13.15 | 31.17 |
| 13.36 | 76.04 |
| 14.44 | 26.62 |
| 14.72 | 44.58 |
| 15.77 | 16.64 |
| 16.74 | 21.4 |
| 16.99 | 16.62 |
| 17.61 | 38.15 |
| 18.40 | 36.03 |

-continued

| 2θ (°) ± 0.2° | intensity % |
|---|---|
| 18.79 | 17.04 |
| 19.28 | 6.78 |
| 19.81 | 35.24 |
| 20.01 | 32.01 |
| 20.46 | 6.51 |
| 21.33 | 21.41 |
| 22.18 | 41.74 |
| 22.84 | 14.89 |
| 23.06 | 18.82 |
| 23.50 | 11.4 |
| 23.73 | 15.87 |
| 24.18 | 27.57 |
| 24.65 | 16.62 |
| 25.00 | 14.2 |
| 25.28 | 25.47 |
| 26.19 | 19.26 |
| 26.46 | 20.68 |
| 27.15 | 6.05 |
| 28.30 | 7.01 |
| 28.94 | 3.36 |
| 29.30 | 4.36 |
| 29.86 | 8.51 |
| 32.38 | 6.44 |
| 33.32 | 9.95 |
| 33.87 | 3.95 |
| 35.56 | 4.07 |
| 37.51 | 2.35 |

Figure 2:
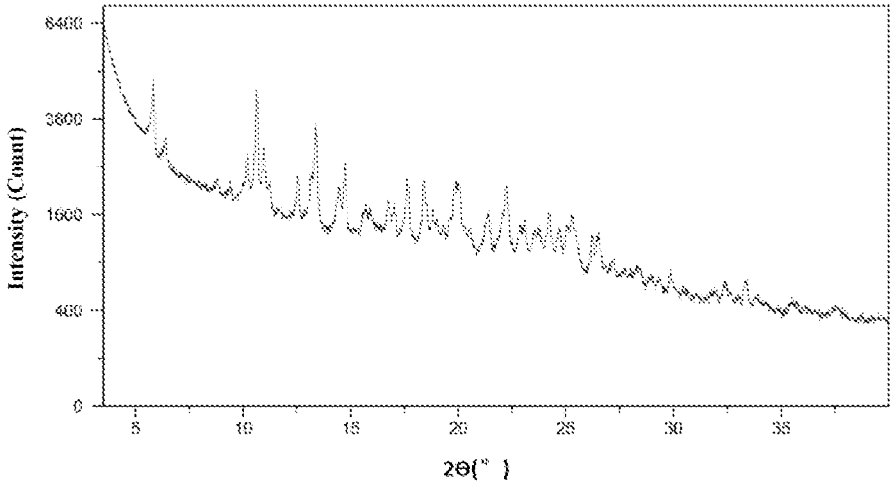
FIG. 2 shows the XRPD pattern of crystal form B of the pamoate of the compound of formula I.

In some embodiments, the crystal form B of the pamoate of the compound of formula I has an XRPD pattern substantially as shown in FIG. 2. In some preferred embodiments, the crystal form B of the pamoate of the compound of formula I has an XRPD pattern as shown in FIG. 2.

Crystal Form C

In some embodiments, provided is a crystal form C of the pamoate of the compound of formula I, wherein the stoichiometric ratio of the compound of formula I to pamoic acid is 1:1, and the crystal form C of the pamoate of the compound of formula I has an XRPD pattern comprising 2θ diffraction peak at about 7.43±0.2°, 11.18±0.2°, 11.98±0.2°, 14.78±0.2°, 20.20±0.2°, 20.97±0.2° and 23.30±0.2°. Preferably, the crystal form C of the pamoate of the compound of formula I has an XRPD pattern I further comprising 2θ diffraction peak at about 16.90±0.2°, 19.73±0.2°, 22.12±0.2° and 25.37±0.2°. Preferably, the crystal form C of the pamoate of the compound of formula I has an XRPD pattern further comprising 2θ diffraction peak at about 19.34±0.2° and 22.91±0.2°.

In some embodiments, the crystal form C of the pamoate of the compound of formula I has an XRPD pattern comprising 2θ diffraction peak at about 7.43±0.2°, 11.18±0.2°, 11.98±0.2°, 14.78±0.2°, 16.90±0.2°, 19.73±0.2°, 20.20±0.2°, 20.97±0.2°, 22.12±0.2°, 23.31±0.2° and 25.37±0.2°. In other embodiments, the crystal form C of the pamoate of the compound of formula I has an XRPD pattern comprising 2θ diffraction peak at about 7.43±0.2°, 11.18±0.2°, 11.98±0.2°, 14.78±0.2°, 16.90±0.2°, 19.34±0.2°, 19.73±0.2°, 20.20±0.2°, 20.97±0.2°, 22.12±0.2°, 22.91±0.2°, 23.31±0.2° and 25.37±0.2°.

In some embodiments, the crystal form C of the pamoate of the compound of formula I has an XRPD pattern comprising the following 2θ diffraction peak at:

| 2θ (°) ± 0.2° | intensity % |
|---|---|
| 6.14 | 10.41 |
| 7.43 | 17.62 |

-continued

| 2θ (°) ± 0.2° | intensity % |
|---|---|
| 10.11 | 2.94 |
| 10.54 | 4.96 |
| 11.18 | 53.18 |
| 11.45 | 15.47 |
| 11.67 | 22.17 |
| 11.98 | 74.3 |
| 13.37 | 11.72 |
| 13.68 | 27.29 |
| 14.78 | 100 |
| 15.09 | 26.67 |
| 15.56 | 19.79 |
| 16.13 | 6.61 |
| 16.61 | 24.64 |
| 16.90 | 34.42 |
| 17.14 | 15.7 |
| 17.56 | 3.03 |
| 17.83 | 21.03 |
| 18.41 | 13.59 |
| 18.72 | 21.32 |
| 19.34 | 51.54 |
| 19.73 | 39.88 |
| 20.20 | 76.83 |
| 20.68 | 13.81 |
| 20.97 | 76.23 |
| 22.12 | 22.49 |
| 22.91 | 40.27 |
| 23.31 | 54.64 |
| 23.52 | 18.37 |
| 24.19 | 11.85 |
| 24.46 | 9.23 |
| 24.94 | 18.48 |
| 25.37 | 27.48 |
| 26.29 | 10.45 |
| 26.67 | 9.81 |
| 27.46 | 9.36 |
| 28.24 | 12.56 |
| 28.95 | 4.45 |
| 29.85 | 17.75 |
| 30.52 | 13.05 |
| 31.56 | 12.89 |
| 32.16 | 8.14 |
| 33.11 | 4.14 |
| 34.26 | 7.77 |
| 34.73 | 11.38 |
| 35.59 | 10.85 |
| 36.79 | 8.54 |
| 38.04 | 5.01 |
| 39.28 | 2.41 |

Figure 3:
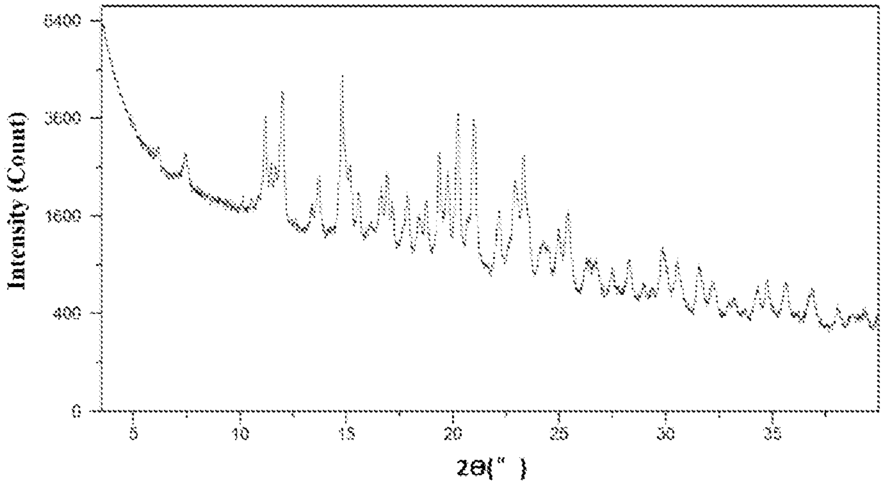
FIG. 3 shows the XRPD pattern of crystal form C of the pamoate of the compound of formula I.

In some embodiments, the crystal form C of the pamoate of the compound of formula I has an XRPD pattern substantially as shown in FIG. 3. In some preferred embodiments, the crystal form C of the pamoate of the compound of formula I has an XRPD pattern as shown in FIG. 3.

Crystal Form D In some embodiments, provided is a crystal form D of the pamoate of the compound of formula I, wherein the stoichiometric ratio of the compound of formula I to pamoic acid is 1:1, and the crystal form D of the pamoate of the compound of formula I has an XRPD pattern comprising 2θ diffraction peak at about 11.24±0.2°, 11.88±0.2°, 12.03±0.2°, 13.57±0.2°, 14.76±0.2°, 15.17±0.2°, 20.85±0.2°, 21.15±0.2° and 23.26±0.2°. Preferably, the crystal form D of the pamoate of the compound of formula I has an XRPD pattern further comprising 2θ diffraction peak at about 15.17±0.2°, 16.92±0.2° and 24.24±0.2°. Preferably, the crystal form D of the pamoate of the compound of formula I has an XRPD pattern further comprising 2θ diffraction peak at about 19.3709±0.2° and 20.2490±0.2°.

In some embodiments, the crystal form D of the pamoate of the compound of formula I has an XRPD pattern comprising 2θ diffraction peak at about 11.24±0.2°, 11.88±0.2°, 12.03±0.2°, 13.57±0.2°, 14.76±0.2°, 15.17±0.2°, 16.92±0.2°, 20.85±0.2°, 21.15±0.2°, 23.26±0.2° and 24.24±0.2°. In other embodiments, the crystal form D of the pamoate of the compound of formula I has an XRPD pattern comprising 2θ diffraction peak at about 11.24±0.2°, 11.88±0.2°, 12.03±0.2°, 13.57±0.2°, 14.76±0.2°, 15.17±0.2°, 16.92±0.2°, 19.37±0.2°, 20.85±0.2°, 21.15±0.2°, 23.26±0.2°, 24.24±0.2° and 20.25±0.2°.

In some embodiments, the crystal form D of the pamoate of the compound of formula I has an XRPD pattern comprising the following 2θ diffraction peak at:

| 2θ (°) ± 0.2° | intensity % |
|---|---|
| 7.33 | 17.63 |
| 7.54 | 15.65 |
| 11.24 | 61.09 |
| 11.88 | 44.05 |
| 12.03 | 70.78 |
| 13.57 | 43.29 |
| 14.76 | 100 |
| 15.17 | 48.71 |
| 15.69 | 14.69 |
| 16.51 | 20 |
| 16.92 | 38.43 |
| 17.39 | 14.84 |
| 17.87 | 27.79 |
| 18.21 | 14.28 |
| 18.90 | 14.2 |
| 19.37 | 34.69 |
| 19.80 | 28.85 |
| 20.25 | 73.87 |
| 20.85 | 40.65 |
| 21.15 | 50.06 |
| 22.25 | 31.28 |
| 22.68 | 18.04 |
| 22.91 | 24.52 |
| 23.26 | 47.86 |
| 23.91 | 17.2 |
| 24.24 | 32.97 |
| 24.85 | 20.41 |
| 25.34 | 10.18 |
| 25.66 | 18.12 |
| 26.39 | 7.83 |
| 27.16 | 17.11 |
| 28.19 | 11.55 |
| 29.07 | 6.96 |
| 29.53 | 18.19 |
| 29.93 | 7.52 |
| 30.84 | 7.97 |
| 31.31 | 9.52 |
| 32.31 | 7.18 |
| 33.25 | 5.85 |
| 34.33 | 20.54 |
| 35.52 | 8.07 |
| 36.11 | 4.81 |
| 36.81 | 9.4 |
| 37.34 | 2.71 |
| 38.51 | 4.7 |

Figure 4:
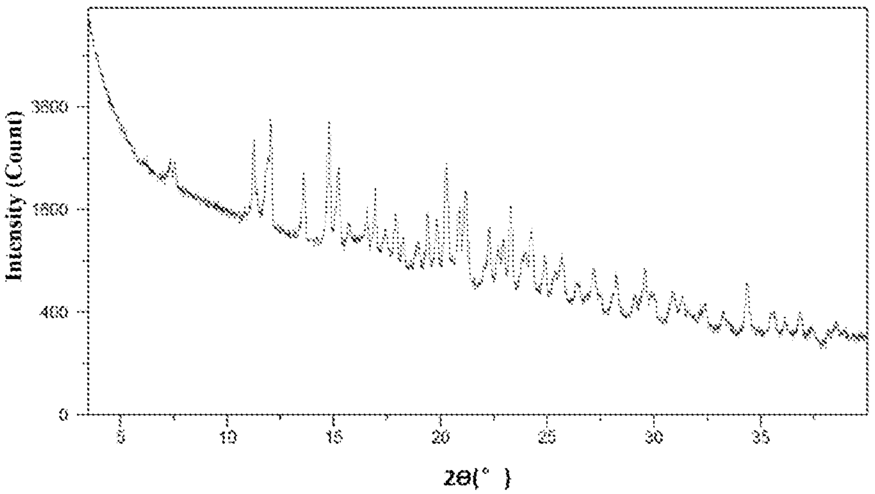
FIG. 4 shows the XRPD pattern of crystal form D of the pamoate of the compound of formula I.

In some embodiments, the crystal form D of the pamoate of the compound of formula I has an XRPD pattern substantially as shown in FIG. 4. In some preferred embodiments, the crystal form D of the pamoate of the compound of formula I has an XRPD pattern as shown in FIG. 4.

Crystal Form E

In some embodiments, provided is a crystal form E of the pamoate of the compound of formula I, wherein the stoichiometric ratio of the compound of formula I to pamoic acid is 1:1, and the crystal form E of the pamoate of the compound of formula I has an XRPD pattern comprising 2θ diffraction peak at about 7.32±0.2°, 11.26±0.2°, 12.04±0.2°, 14.77±0.2°, 15.24±0.2°, 16.95±0.2°, 20.2±0.2°, 21.26±0.2°, and 23.27±0.2°. Preferably, the crystal form E of the pamoate of the compound of formula I has an XRPD pattern further comprising 2θ diffraction peak at about 19.37±0.2° and 19.83±0.2°.

In some embodiments, the crystal form B of the pamoate of the compound of formula I has an XRPD pattern comprising the following 2θ diffraction peak at:

| 2θ (°) ± 0.2° | intensity % |
|---|---|
| 7.32 | 11.94 |
| 7.58 | 11.53 |
| 11.26 | 87.17 |
| 12.04 | 84.85 |
| 13.60 | 25.62 |
| 14.77 | 80.63 |
| 15.24 | 31.61 |
| 15.72 | 15.9 |
| 16.55 | 16.49 |
| 16.95 | 31.68 |
| 17.49 | 11.08 |
| 17.93 | 18.75 |
| 18.19 | 11.48 |
| 19.36 | 29.35 |
| 19.83 | 32.4 |
| 20.28 | 100 |
| 20.87 | 23.47 |
| 21.26 | 31.12 |
| 22.26 | 33.82 |
| 22.89 | 14.51 |
| 23.27 | 55.73 |
| 23.95 | 22.75 |
| 24.27 | 28.78 |
| 24.85 | 13.82 |
| 25.38 | 10.39 |
| 25.85 | 8.62 |
| 27.19 | 14.51 |
| 28.22 | 12.01 |
| 29.07 | 7.97 |
| 29.55 | 11.1 |
| 29.95 | 7.55 |
| 31.26 | 7.97 |
| 31.65 | 4.64 |
| 32.34 | 9.85 |
| 33.21 | 7.11 |
| 34.33 | 15.66 |
| 35.50 | 8.11 |
| 36.79 | 10.12 |

Figure 5:
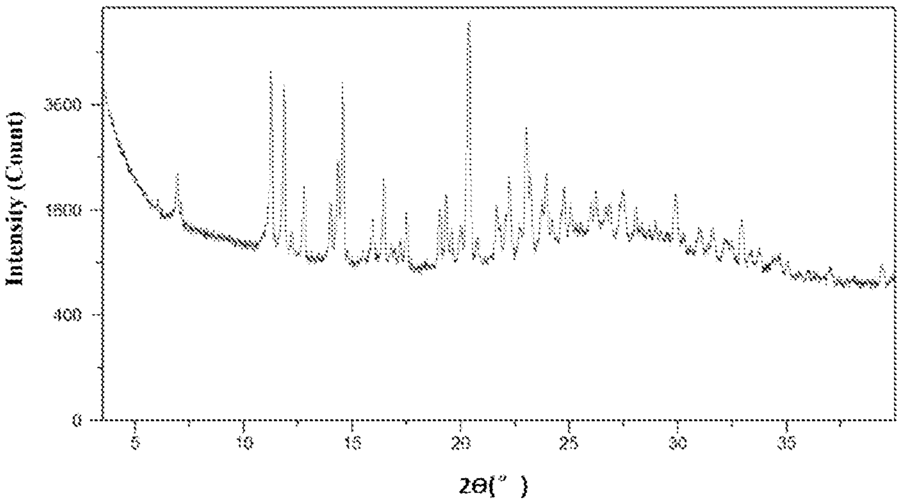
FIG. 5 shows the XRPD pattern of crystal form E of the pamoate of the compound of formula I.

In some embodiments, the crystal form E of the pamoate of the compound of formula I has an XRPD pattern substantially as shown in FIG. 5. In some preferred embodiments, the crystal form E of the pamoate of the compound of formula I has an XRPD pattern as shown in FIG. 5.

Crystal Form F

In some embodiments, provided is a crystal form F of the pamoate of the compound of formula I, wherein the stoichiometric ratio of the compound of formula I to pamoic acid is 1:1, and the crystal form F of the pamoate of the compound of formula I has an XRPD pattern comprising 2θ diffraction peak at about 11.19±0.2°, 12.10±0.2°, 14.67±0.2°, 15.48±0.2°, 18.11±0.2°, 20.25±0.2° and 23.33±0.2°. Preferably, the crystal form F of the pamoate of the compound of formula I has an XRPD pattern further comprising 2θ diffraction peak at about 11.92±0.2°, 14.67±0.2°, 16.71±0.2° and 25.84±0.2°. Preferably, the crystal form F of the pamoate of the compound of formula I has an XRPD pattern further comprising 2θ diffraction peak at about 19.19±0.2° and 21.23±0.2°.

In some embodiments, the crystal form F of the pamoate of the compound of formula I has an XRPD pattern comprising 2θ diffraction peak at about 11.19±0.2°, 11.92±0.2°, 12.10±0.2°, 14.67±0.2°, 15.48±0.2°, 16.71±0.2°, 18.11±0.2°, 20.25±0.2°, 23.33±0.2° and 25.84±0.2°. In some embodiments, the crystal form F of the pamoate of the compound of formula I has an XRPD pattern comprising 2θ diffraction peak at about 11.19±0.2°, 11.92±0.2°, 12.10±0.2°, 14.67±0.2°, 15.48±0.2°, 16.71±0.2°, 18.11±0.2°, 19.19±0.2°, 20.25±0.2°, 21.23±0.2°, 23.33±0.2° and 25.84±0.2°.

In some embodiments, the crystal form F of the pamoate of the compound of formula I has an XRPD pattern comprising the following 2θ diffraction peak at:

| 2θ (°) ± 0.2° | intensity % |
|---|---|
| 6.17 | 30.22 |
| 7.35 | 23.57 |
| 11.19 | 72.48 |
| 11.92 | 85.65 |
| 12.10 | 79.72 |
| 13.78 | 46.64 |
| 14.67 | 80.22 |
| 14.84 | 46.68 |
| 15.48 | 100 |
| 16.71 | 79.17 |
| 17.44 | 26.4 |
| 18.11 | 64.47 |
| 18.75 | 6.32 |
| 19.19 | 57.73 |
| 19.78 | 42.76 |
| 20.25 | 69.24 |
| 21.23 | 61.03 |
| 21.39 | 46.85 |
| 22.28 | 18.46 |
| 22.91 | 24.46 |
| 23.33 | 69.75 |
| 24.02 | 32.91 |
| 24.35 | 23.03 |
| 24.67 | 10.23 |
| 25.24 | 21 |
| 25.84 | 33.43 |
| 26.95 | 25.88 |
| 28.29 | 8.74 |
| 29.57 | 8.79 |
| 29.81 | 16.98 |
| 31.07 | 30.5 |
| 31.58 | 9.24 |
| 32.44 | 4.34 |
| 33.04 | 8.18 |
| 34.24 | 12.08 |
| 35.29 | 7.02 |
| 35.67 | 5.37 |
| 36.59 | 10.53 |
| 38.20 | 5.21 |
| 38.98 | 2.98 |

Figure 6:
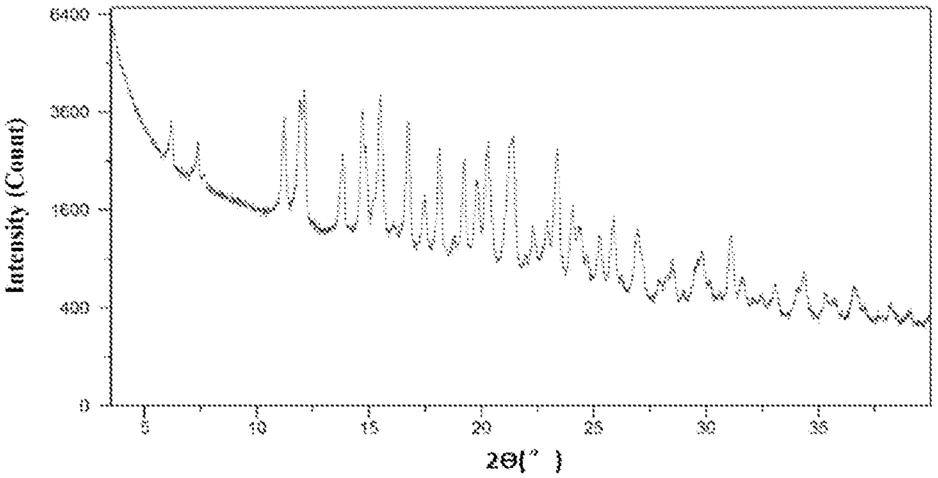
FIG. 6 shows the XRPD pattern of crystal form F of the pamoate of the compound of formula I.

In some embodiments, the crystal form F of the pamoate of the compound of formula I has an XRPD pattern substantially as shown in FIG. 6. In some preferred embodiments, the crystal form F of the pamoate of the compound of formula I has an XRPD pattern as shown in FIG. 6.

Crystal Form G

In some embodiments, provided is a crystal form G of the pamoate of the compound of formula I, wherein the stoichiometric ratio of the compound of formula I to pamoic acid is 1:1, and the crystal form G of the pamoate of the compound of formula I has an XRPD pattern comprising 2θ diffraction peak at about 6.13±0.2°, 11.24±0.2°, 11.86±0.2°, 13.15±0.2°, 14.79±0.2°, 20.27±0.2° and 23.13±0.2°. Preferably, the crystal form G of the pamoate of the compound of formula I has an XRPD pattern further comprising 2θ diffraction peak at about 11.24±0.2°, 14.54±0.2°, 19.90±0.2°, 20.09±0.2°, 22.21±0.2°, 23.96±0.2° and 24.76±0.2°. More preferably, the crystal form G of the pamoate of the compound of formula I has an XRPD pattern further comprising 2θ diffraction peak at about 16.88±0.2°, 19.35±0.2° and 20.46±0.2°.

In some embodiments, the crystal form G of the pamoate of the compound of formula I has an XRPD pattern comprising 2θ diffraction peak at about 6.13±0.2°, 11.24±0.2°, 11.86±0.2°, 13.15±0.2°, 14.54±0.2°, 14.79±0.2°, 19.90±0.2°, 20.09±0.2°, 20.27±0.2°, 22.21±0.2°, 23.13±0.2°, 23.96±0.2° and 24.76±0.2°. In other embodiments, the crystal form G of the pamoate of the compound of formula I has an XRPD pattern comprising 2θ diffraction peak at about 6.13±0.2°, 11.24±0.2°, 11.86±0.2°, 13.15±0.2°, 14.54±0.2°, 14.79±0.2°, 16.88±0.2°, 19.35±0.2°, 19.90±0.2°, 20.09±0.2°, 20.27±0.2°, 20.46±0.2°, 22.21±0.2°, 23.13±0.2°, 23.96±0.2° and 24.76±0.2°.

In some embodiments, the crystal form G of the pamoate of the compound of formula I has an XRPD pattern comprising the following 2θ diffraction peak at:

| 2θ (°) ± 0.2° | intensity % |
|---|---|
| 6.13 | 12.63 |
| 7.19 | 16.58 |
| 11.24 | 55.6 |
| 11.86 | 97.1 |
| 12.35 | 7.2 |
| 13.15 | 39.8 |
| 14.54 | 57.44 |
| 14.79 | 59.37 |
| 15.57 | 13.54 |
| 16.20 | 21.8 |
| 16.88 | 44.18 |
| 17.35 | 28.19 |
| 18.13 | 14.33 |
| 19.35 | 40.06 |
| 19.90 | 33.15 |
| 20.09 | 33.8 |
| 20.27 | 100 |
| 20.46 | 76.23 |
| 22.21 | 84.09 |
| 22.88 | 18.86 |
| 23.13 | 65.96 |
| 23.96 | 53.32 |
| 24.76 | 42.38 |
| 25.27 | 20.94 |
| 26.33 | 14.68 |
| 26.65 | 7.43 |
| 27.15 | 14.2 |
| 27.74 | 28.07 |
| 28.28 | 12.12 |
| 29.04 | 19.09 |
| 29.90 | 16.93 |
| 31.18 | 4.98 |
| 31.57 | 6.99 |
| 32.21 | 6.65 |
| 32.83 | 6.04 |
| 33.41 | 5.3 |
| 34.22 | 15.41 |
| 35.20 | 5.44 |
| 36.87 | 4.51 |
| 38.46 | 5.16 |

Figure 7:
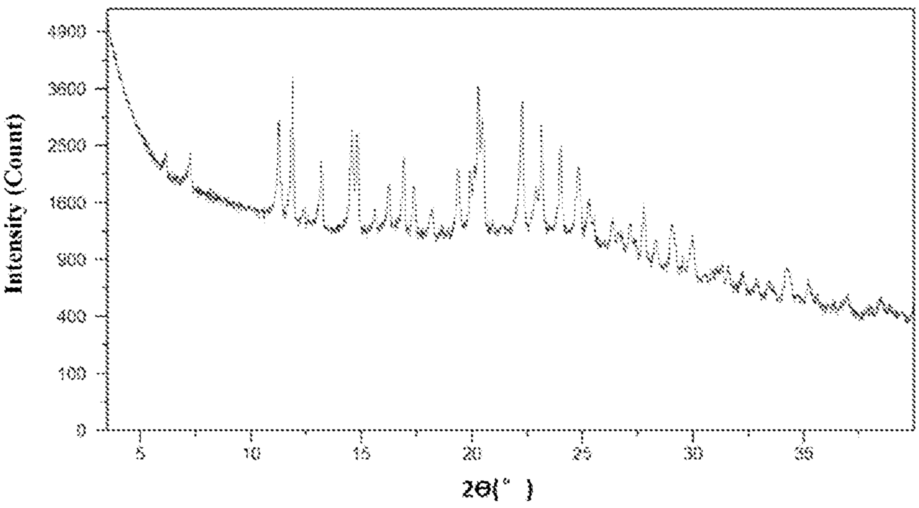
FIG. 7 shows the XRPD pattern of crystal form G of the pamoate of the compound of formula I.

In some embodiments, the crystal form G of the pamoate of the compound of formula I has an XRPD pattern substantially as shown in FIG. 7. In some preferred embodiments, the crystal form G of the pamoate of the compound of formula I has an XRPD pattern as shown in FIG. 7.

Crystal Form H

In some embodiments, provided is a crystal form H of the pamoate of the compound of formula I, wherein the stoichiometric ratio of the compound of formula I to pamoic acid is 1:1, and the crystal form H of the pamoate of the compound of formula I has an XRPD pattern comprising 2θ diffraction peak at about 7.08±0.2°, 11.92±0.2°, 13.03±0.2°, 14.71±0.2°, 16.90±0.2°, 20.85±0.2°, 21.96±0.2°, 23.04±0.2° and 23.56±0.2°. Preferably, the crystal form H of the pamoate of the compound of formula I has an XRPD pattern further comprising 2θ diffraction peak at about 11.76±0.2°, 13.03±0.2°, 20.27±0.2° and 26.66±0.2°. More preferably, the crystal form H of the pamoate of the compound of formula I has an XRPD pattern further comprising 2θ diffraction peak at about 11.30±0.2°, 14.71±0.2° and 19.97±0.2°.

In some embodiments, the crystal form H of the pamoate of the compound of formula I has an XRPD pattern comprising 2θ diffraction peak at about 7.08±0.2°, 11.76±0.2°, 11.92±0.2°, 13.03±0.2°, 14.71±0.2°, 16.90±0.2°, 20.27±0.2°, 20.85±0.2°, 21.96±0.2°, 23.04±0.2°, 23.56±0.2° and 26.66±0.2°. In other embodiments, the crystal form H of the pamoate of the compound of formula I has an XRPD pattern comprising 2θ diffraction peak at about 7.08±0.2°, 11.76±0.2°, 11.30±0.2°, 11.92±0.2°, 13.03±0.2°, 14.71±0.2°, 16.90±0.2°, 19.97±0.2°, 20.27±0.2°, 20.85±0.2°, 21.96±0.2°, 23.04±0.2°, 23.56±0.2° and 26.66±0.2°.

In some embodiments, the crystal form H of the pamoate of the compound of formula I has an XRPD pattern comprising the following 2θ diffraction peak at:

| 2θ (°) ± 0.2° | intensity % |
|---|---|
| 6.26 | 8.71 |
| 7.08 | 25.59 |
| 7.34 | 2.15 |
| 11.30 | 28.73 |
| 11.76 | 24.55 |
| 11.92 | 78.74 |
| 12.62 | 8.51 |
| 13.03 | 33.14 |
| 14.29 | 16.25 |
| 14.71 | 100 |
| 16.11 | 30.48 |
| 16.90 | 47.33 |
| 17.14 | 17.24 |
| 17.46 | 15.68 |
| 17.87 | 10.99 |
| 18.56 | 9.59 |
| 19.03 | 11.32 |
| 19.39 | 16.92 |
| 19.97 | 30.49 |
| 20.27 | 60.84 |
| 20.85 | 66.48 |
| 21.27 | 8.57 |
| 21.96 | 54.69 |
| 22.17 | 28.39 |
| 22.30 | 22.48 |
| 23.04 | 40.88 |
| 23.56 | 41.52 |
| 23.79 | 20.91 |
| 24.06 | 30.13 |
| 24.68 | 11.47 |
| 25.43 | 39.08 |
| 25.82 | 15.27 |
| 26.16 | 5.19 |
| 26.66 | 32.98 |
| 27.25 | 13.71 |
| 27.69 | 24.91 |
| 28.03 | 6.75 |
| 28.53 | 28.75 |
| 28.85 | 6.51 |
| 29.29 | 8.73 |
| 29.91 | 9.57 |
| 30.42 | 5.51 |
| 30.79 | 13.77 |
| 31.44 | 7.51 |
| 32.01 | 3.9 |
| 32.26 | 5.09 |
| 33.50 | 15.44 |

Figure 8:
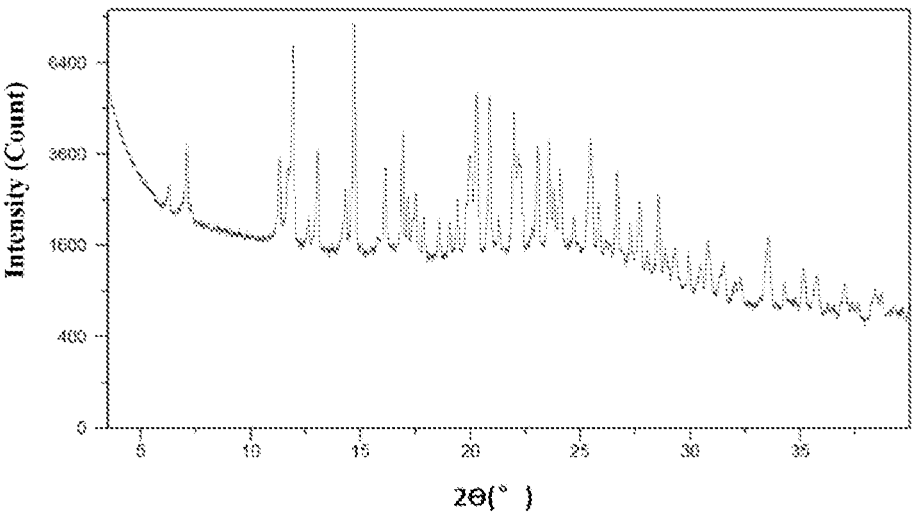
FIG. 8 shows the XRPD pattern of crystal form H of the pamoate of the compound of formula I.

In some embodiments, the crystal form H of the pamoate of the compound of formula I has an XRPD pattern substantially as shown in FIG. 8. In some preferred embodiments, the crystal form H of the pamoate of the compound of formula I has an XRPD pattern as shown in FIG. 8.

Crystal Form I

In some embodiments, provided is a crystal form I of the pamoate of the compound of formula I, wherein the stoichiometric ratio of the compound of formula I to pamoic acid is 1:1, and the crystal form I of the pamoate of the compound of formula I has an XRPD pattern comprising 2θ diffraction peak at about 5.59±0.2°, 5.98±0.2°, 9.39±0.2°, 20.39±0.2°, 25.27±0.2°, and 26.01±0.2°. Preferably, the crystal form I of the pamoate of the compound of formula I has an XRPD pattern further comprising 2θ diffraction peak at about 7.62±0.2°, 8.22±0.2°, 11.59±0.2°, 18.09±0.2° and 22.59±0.2°. More preferably, the crystal form I of the pamoate of the compound of formula I has an XRPD pattern further comprising 2θ diffraction peak at about 7.80±0.2°, 9.88±0.2° and 23.40±0.2°.

In some embodiments, the crystal form I of the pamoate of the compound of formula I has an XRPD pattern comprising 2θ diffraction peak at about 5.59±0.2°, 5.98±0.2°, 7.62±0.2°, 8.22±0.2°, 9.39±0.2°, 11.59±0.2°, 18.09±0.2°, 20.39±0.2°, 22.59±0.2°, 25.27±0.2°, and 26.01±0.2°. In other embodiments, the crystal form I of the pamoate of the compound of formula I has an XRPD pattern comprising 2θ diffraction peak at about 5.59±0.2°, 5.98±0.2°, 7.62±0.2°, 7.80±0.2°, 8.22±0.2°, 9.39±0.2°, 9.88±0.2°, 11.59±0.2°, 18.09±0.2°, 20.39±0.2°, 22.59±0.2°, 23.40±0.2°, 25.27±0.2°, and 26.01±0.2°.

In some embodiments, the crystal form I of the pamoate of the compound of formula I has an XRPD pattern comprising the following 2θ diffraction peak at:

| 2θ (°) ± 0.2° | intensity % |
|---|---|
| 5.59 | 59.67 |
| 5.98 | 39.04 |
| 7.62 | 28.24 |
| 7.80 | 31.25 |
| 8.22 | 34.39 |
| 9.39 | 72.02 |
| 9.88 | 32.2 |
| 11.13 | 18.93 |
| 11.59 | 30.15 |
| 12.10 | 12.8 |
| 12.52 | 17.9 |
| 12.84 | 10.94 |
| 13.32 | 7.36 |
| 14.44 | 12.69 |
| 15.67 | 16.3 |
| 16.06 | 13.57 |
| 16.67 | 23.35 |
| 17.48 | 23.57 |
| 18.09 | 42.54 |
| 19.01 | 17.3 |
| 19.91 | 21.88 |
| 20.39 | 33.49 |
| 20.95 | 3.15 |
| 22.02 | 13.49 |
| 22.59 | 25.91 |
| 22.88 | 18.16 |
| 23.40 | 37.95 |
| 24.06 | 7.39 |
| 24.73 | 12.19 |
| 25.27 | 100 |
| 26.01 | 49.2 |
| 26.46 | 17.61 |
| 26.67 | 11.1 |
| 29.56 | 8.3 |
| 31.16 | 7.15 |
| 32.57 | 2.63 |
| 34.32 | 2.95 |
| 36.36 | 2.55 |
| 38.68 | 2.28 |

-continued

Figure 9:
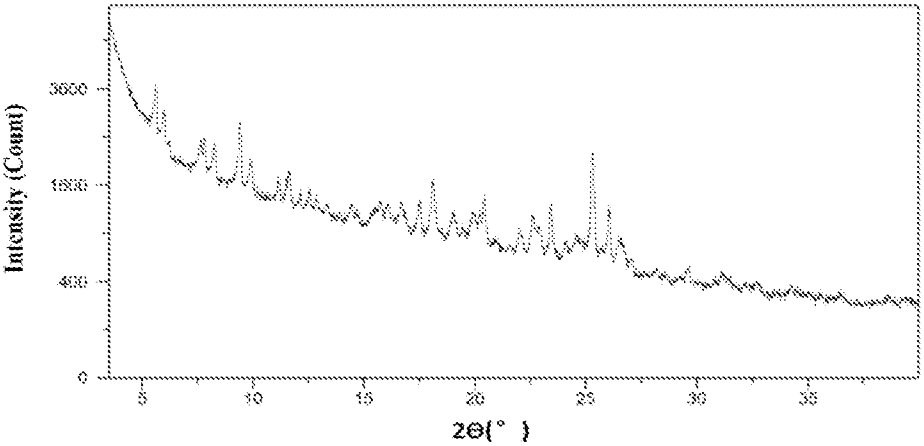
FIG. 9 shows the XRPD pattern of crystal form I of the pamoate of the compound of formula I.

In some embodiments, the crystal form I of the pamoate of the compound of formula I has an XRPD pattern substantially as shown in FIG. 9. In some preferred embodiments, the crystal form I of the pamoate of the compound of formula I has an XRPD pattern as shown in FIG. 9.

Crystal Form J

In some embodiments, provided is a crystal form J of the pamoate of the compound of formula I, wherein the stoichiometric ratio of the compound of formula I to pamoic acid is 1:1, and the crystal form J of the pamoate of the compound of formula I has an XRPD pattern comprising 2θ diffraction peak at about 5.33±0.2°, 7.13±0.2°, 10.90±0.2°, 14.57±0.2°, 16.62±0.2°, 19.80±0.2° and 25.29±0.2°. Preferably, the crystal form J of the pamoate of the compound of formula I has an XRPD pattern further comprising 2θ diffraction peak at about 14.99±0.2°, 19.01±0.2° and 20.74±0.2°. More preferably, the crystal form J of the pamoate of the compound of formula I has an XRPD pattern further comprising 2θ diffraction peak at about 19.32±0.2° and 22.24±0.2°.

In some embodiments, the crystal form J of the pamoate of the compound of formula I has an XRPD pattern comprising 2θ diffraction peak at about 5.33±0.2°, 7.13±0.2°, 10.90±0.2°, 14.57±0.2°, 14.99±0.2°, 16.62±0.2°, 19.01±0.2°, 19.80±0.2°, 20.74±0.2° and 25.29±0.2°. In other embodiments, the crystal form J of the pamoate of the compound of formula I has an XRPD pattern comprising 2θ diffraction peak at about 5.33±0.2°, 7.13±0.2°, 10.90±0.2°, 14.57±0.2°, 14.99±0.2°, 16.62±0.2°, 19.01±0.2°, 19.32±0.2°, 19.80±0.2°, 20.74±0.2°, 22.24±0.2° and 25.29±0.2°.

In some embodiments, the crystal form J of the pamoate of the compound of formula I has an XRPD pattern comprising the following 2θ diffraction peak at:

| 2θ (°) ± 0.2° | intensity % |
|---|---|
| 5.33 | 79.42 |
| 7.13 | 14.19 |
| 8.18 | 5.21 |
| 10.90 | 81.48 |
| 12.90 | 6.35 |
| 14.57 | 73.96 |
| 14.99 | 50.46 |
| 16.07 | 11.52 |
| 16.62 | 42.67 |
| 17.24 | 18.39 |
| 18.20 | 7.4 |
| 18.62 | 14.39 |
| 19.01 | 46.44 |
| 19.32 | 84.3 |
| 19.80 | 100 |
| 20.22 | 53.7 |
| 20.74 | 73.06 |
| 21.65 | 15.04 |
| 22.24 | 33.93 |
| 22.99 | 22.42 |
| 23.15 | 22.54 |
| 23.69 | 14.78 |
| 25.29 | 25.25 |
| 26.17 | 4.77 |
| 26.65 | 7.43 |
| 27.50 | 7.93 |
| 28.99 | 5.49 |
| 29.39 | 5.67 |

-continued

| 2θ (°) ± 0.2° | intensity % |
|---|---|
| 30.81 | 6.71 |
| 31.59 | 2.04 |
| 32.05 | 7.35 |
| 33.31 | 6.64 |
| 33.94 | 4 |
| 34.66 | 7.94 |
| 36.61 | 1.99 |
| 38.98 | 3.87 |

Figure 10:
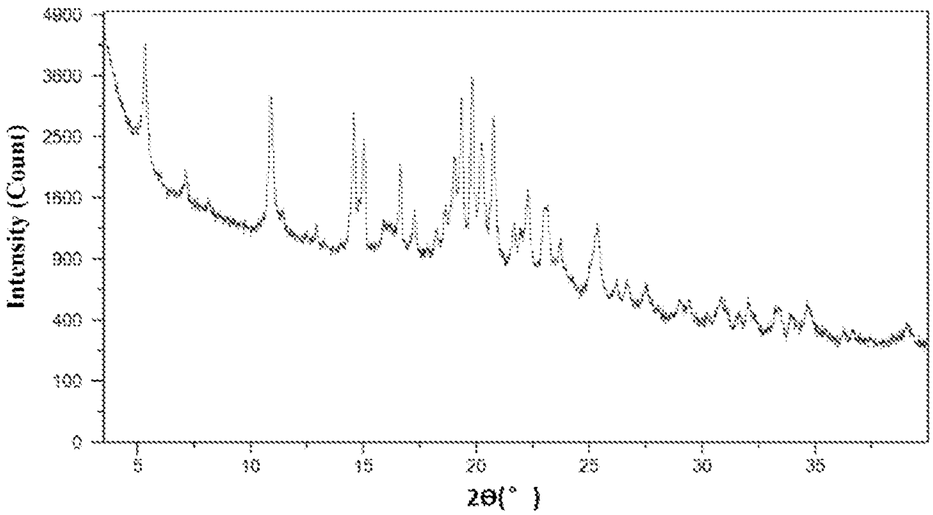
FIG. 10 shows the XRPD pattern of crystal form J of the pamoate of the compound of formula I.

In some embodiments, the crystal form J of the pamoate of the compound of formula I has an XRPD pattern substantially as shown in FIG. 10. In some preferred embodiments, the crystal form J of the pamoate of the compound of formula I has an XRPD pattern as shown in FIG. 10.

Crystal Form K

In some embodiments, provided is a crystal form K of the pamoate of the compound of formula I, wherein the stoichiometric ratio of the compound of formula I to pamoic acid is 1:1, and the crystal form K of the pamoate of the compound of formula I has an XRPD pattern comprising 2θ diffraction peak at about 5.57±0.2°, 5.97±0.2°, 7.73±0.2°, 11.55±0.2°, 18.01±0.2°, and 18.90±0.2°. Preferably, the crystal form K of the pamoate of the compound of formula I has an XRPD pattern further comprising 2θ diffraction peak at about 9.34±0.2°, 19.79±0.2° and 25.84±0.2°. More preferably, the crystal form K of the pamoate of the compound of formula I has an XRPD pattern further comprising 2θ diffraction peak at about 23.25±0.2° and 25.10±0.2°.

In some embodiments, the crystal form K of the pamoate of the compound of formula I has an XRPD pattern comprising 2θ diffraction peak at about 5.57±0.2°, 5.97±0.2°, 7.73±0.2°, 9.34±0.2°, 11.55±0.2°, 18.01±0.2°, 18.90±0.2°, 19.79±0.2° and 25.84±0.2°. In some embodiments, the crystal form K of the pamoate of the compound of formula I has an XRPD pattern comprising 2θ diffraction peak at about 5.57±0.2°, 5.97±0.2°, 7.73±0.2°, 9.34±0.2°, 11.55±0.2°, 18.01±0.2°, 18.90±0.2°, 19.79±0.2°, 23.25±0.2°, 25.10±0.2° and 25.84±0.2°.

In some embodiments, the crystal form K of the pamoate of the compound of formula I has an XRPD pattern comprising the following 2θ diffraction peak at:

| 2θ (°) ± 0.2° | intensity % |
|---|---|
| 5.57 | 65.79 |
| 5.97 | 34.85 |
| 7.73 | 37.12 |
| 8.20 | 35.58 |
| 9.34 | 82.2 |
| 9.83 | 31.67 |
| 11.09 | 19.52 |
| 11.55 | 40.48 |
| 12.04 | 13.16 |
| 12.46 | 7.79 |
| 13.30 | 11.44 |
| 14.39 | 11.32 |
| 15.63 | 16.75 |
| 15.99 | 23.11 |
| 16.56 | 14.28 |
| 17.38 | 22.61 |
| 18.01 | 43.29 |
| 18.90 | 16.71 |
| 19.79 | 25.34 |
| 20.04 | 17.51 |
| 20.28 | 33.4 |
| 22.44 | 17.16 |
| 22.70 | 13.28 |

-continued

| 2θ (°) ± 0.2° | intensity % |
|---|---|
| 23.25 | 30.25 |
| 24.54 | 14.57 |
| 25.10 | 100 |
| 25.84 | 36.13 |
| 26.29 | 8.26 |
| 26.53 | 11.06 |
| 26.61 | 3.5 |
| 36.92 | 3.51 |

Figure 11:
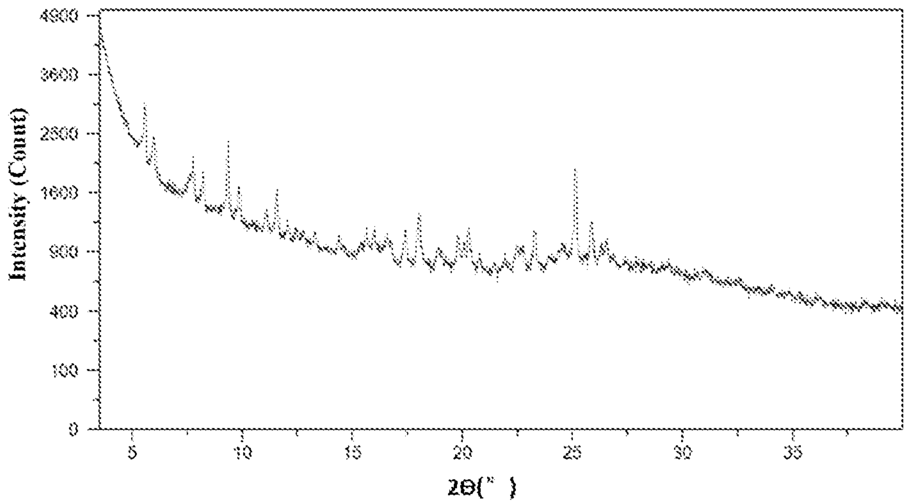
FIG. 11 shows the XRPD pattern of crystal form K of the pamoate of the compound of formula I.

In some embodiments, the crystal form K of the pamoate of the compound of formula I has an XRPD pattern substantially as shown in FIG. 11. In some preferred embodiments, the crystal form K of the pamoate of the compound of formula I has an XRPD pattern as shown in FIG. 11.

Crystal Form L

In some embodiments, provided is a crystal form L of the pamoate of the compound of formula I, wherein the stoichiometric ratio of the compound of formula I to pamoic acid is 1:1, and the crystal form L of the pamoate of the compound of formula I has an XRPD pattern comprising 2θ diffraction peak at about 6.20±0.2°, 8.13±0.2°, 9.92±0.2°, 10.85±0.2°, 12.81±0.2°, and 21.82±0.2°. Preferably, the crystal form L of the pamoate of the compound of formula I has an XRPD pattern further comprising 2θ diffraction peak at about 15.2±0.2° and 25.86±0.2°. More preferably, the crystal form L of the pamoate of the compound of formula I has an XRPD pattern further comprising 2θ diffraction peak at about 19.29±0.2° and 25.63±0.2°.

In some embodiments, the crystal form L of the pamoate of the compound of formula I has an XRPD pattern comprising 2θ diffraction peak at about 6.20±0.2°, 8.13±0.2°, 9.92±0.2°, 10.8±0.2°, 12.81±0.2°, 15.29±0.2°, 21.8±0.2° and 25.86±0.2°. In other embodiments, the crystal form L of the pamoate of the compound of formula has an XRPD pattern comprising 2θ diffraction peak at about 6.20±0.2°, 8.13±0.2°, 9.92±0.2°, 10.85±0.2°, 12.81±0.2°, 15.29±0.2°, 19.29±0.2°, 21.82±0.2°, 25.63±0.2° and 25.86±0.2°.

In some embodiments, the crystal form L of the pamoate of the compound of formula I has an XRPD pattern comprising the following 2θ diffraction peak at:

| 2θ (°) ± 0.2° | intensity % |
|---|---|
| 6.20 | 100 |
| 8.13 | 31.49 |
| 9.64 | 14.78 |
| 9.92 | 27.65 |
| 10.85 | 17.17 |
| 11.25 | 4.9 |
| 12.81 | 16.89 |
| 13.32 | 11.24 |
| 13.53 | 7.43 |
| 15.01 | 7.89 |
| 15.29 | 14.61 |
| 15.72 | 6.9 |
| 16.38 | 16.19 |
| 17.19 | 4.7 |
| 17.47 | 7.79 |
| 17.98 | 6.6 |
| 18.54 | 18.95 |
| 18.86 | 13.68 |
| 19.29 | 23.83 |
| 19.93 | 12.28 |
| 20.93 | 4.98 |
| 21.28 | 21.64 |
| 21.82 | 11.99 |
| 22.52 | 9.65 |

-continued

| 2θ (°) ± 0.2° | intensity % |
|---|---|
| 22.85 | 5.94 |
| 24.41 | 3.09 |
| 24.75 | 6.97 |
| 25.01 | 6.55 |
| 25.63 | 12.28 |
| 25.86 | 21.17 |
| 26.43 | 2.16 |
| 27.64 | 15.96 |
| 28.45 | 2.95 |
| 29.67 | 1.61 |
| 30.52 | 2.08 |
| 32.00 | 1.99 |
| 32.93 | 1.73 |
| 33.81 | 2.48 |
| 35.57 | 0.94 |
| 36.90 | 0.94 |
| 38.12 | 1.73 |
| 39.43 | 1.29 |

Figure 12:
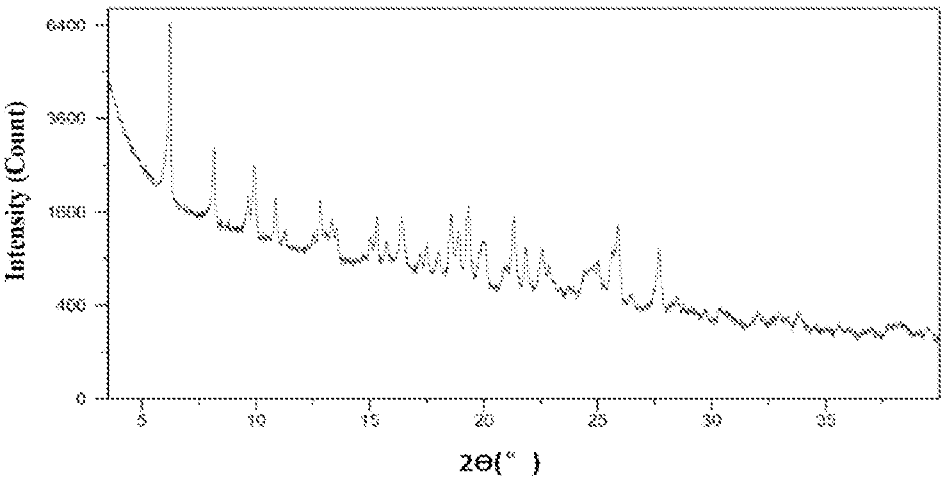
FIG. 12 shows the XRPD pattern of crystal form L of the pamoate of the compound of formula I.

In some embodiments, the crystal form L of the pamoate of the compound of formula I has an XRPD pattern substantially as shown in FIG. 12. In some preferred embodiments, the crystal form L of the pamoate of the compound of formula I has an XRPD pattern as shown in FIG. 12.

Crystal Form M

In some embodiments, provided is a crystal form M of the pamoate of the compound of formula I, wherein the stoichiometric ratio of the compound of formula I to pamoic acid is 1:1, and the crystal form M of the pamoate of the compound of formula I has an XRPD pattern comprising 2θ diffraction peak at about 6.31±0.2°, 11.55±0.2°, 14.49±0.2°, 15.94±0.2°, 19.58±0.2°, and 23.50±0.2°. Preferably, the crystal form M of the pamoate of the compound of formula I has an XRPD pattern further comprising 2θ diffraction peak at about 19.27±0.2°, 20.28±0.2° and 25.88±0.2°. More preferably, the crystal form M of the pamoate of the compound of formula I has an XRPD pattern further comprising 2θ diffraction peak at about 22.27±0.2° and 24.88±0.2°.

In some embodiments, the crystal form M of the pamoate of the compound of formula I has an XRPD pattern comprising 2θ diffraction peak at about 6.31±0.2°, 11.55±0.2°, 14.49±0.2°, 15.94±0.2°, 19.58±0.2°, 19.27±0.2°, 20.28±0.2°, 23.50±0.2° and 25.88±0.2°. In other embodiments, the crystal form M of the pamoate of the compound of formula I has an XRPD pattern comprising 2θ diffraction peak at about 6.31±0.2°, 11.55±0.2°, 14.49±0.2°, 15.94±0.2°, 19.58±0.2°, 19.27±0.2°, 20.28±0.2°, 22.27±0.2°, 23.50±0.2°, 24.88±0.2° and 25.88±0.2°.

In some embodiments, the crystal form M of the pamoate of the compound of formula I has an XRPD pattern comprising the following 2θ diffraction peak at:

| 2θ (°) ± 0.2° | intensity % |
|---|---|
| 6.31 | 21.24 |
| 11.14 | 10.1 |
| 11.55 | 37.28 |
| 12.55 | 11.35 |
| 12.91 | 7.03 |
| 13.91 | 2.64 |
| 14.49 | 100 |
| 14.74 | 7.63 |
| 15.94 | 38.13 |
| 16.68 | 14.75 |
| 17.02 | 2.56 |
| 18.48 | 1.82 |
| 19.27 | 62.08 |

-continued

| 2θ (°) ± 0.2° | intensity % |
|---|---|
| 19.58 | 48.53 |
| 20.28 | 56.15 |
| 21.39 | 2.46 |
| 21.77 | 7.43 |
| 22.27 | 29.88 |
| 22.74 | 3.33 |
| 23.26 | 14.69 |
| 23.50 | 10.26 |
| 24.26 | 16.36 |
| 24.50 | 5.83 |
| 24.88 | 13.61 |
| 25.26 | 5.66 |
| 25.49 | 6.92 |
| 25.88 | 11.39 |
| 27.48 | 6.78 |
| 28.11 | 0.48 |
| 29.31 | 4.42 |
| 29.66 | 4.51 |
| 29.99 | 5.13 |
| 30.62 | 4.07 |
| 30.89 | 4.28 |
| 31.23 | 5.24 |
| 31.89 | 3.41 |
| 33.71 | 10.06 |
| 33.95 | 11.64 |
| 34.54 | 1.68 |
| 35.27 | 3.61 |
| 37.35 | 2.44 |
| 38.58 | 0.87 |
| 39.08 | 2.58 |
| 24.50 | 5.83 |

Figure 13:
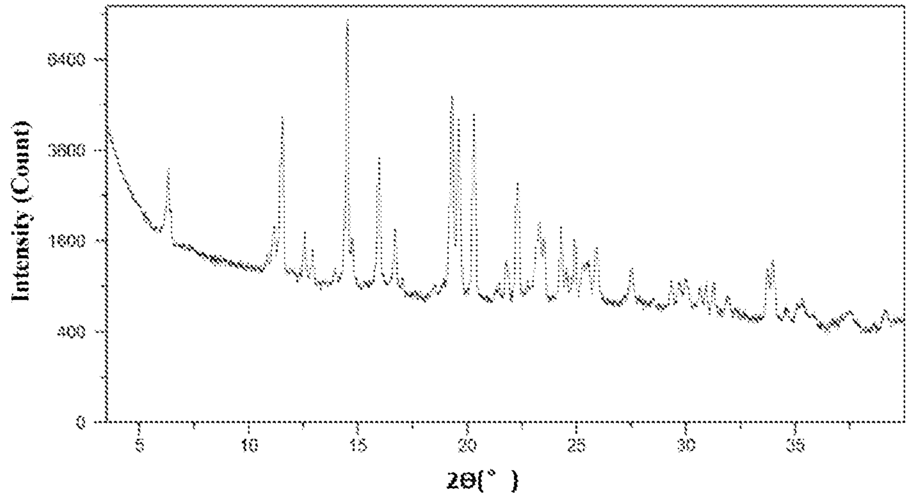
FIG. 13 shows the XRPD pattern of crystal form M of the pamoate of the compound of formula I.

In some embodiments, the crystal form M of the pamoate of the compound of formula I has an XRPD pattern substantially as shown in FIG. 13. In some preferred embodiments, the crystal form M of the pamoate of the compound of formula I has an XRPD pattern as shown in FIG. 13.

Pamoate of the Compound of Formula I and Crystal Form Thereof (2:1)

In some embodiments, the stoichiometric ratio of the compound of formula I to pamoic acid in the pamoate of the compound of formula I is 2:1.

Crystal Form N

In some embodiments, provided is a crystal form N of the pamoate of the compound of formula I, wherein the stoichiometric ratio of the compound of formula I to pamoic acid is 2:1, and the crystal form N of the pamoate of the compound of formula I has an XRPD pattern comprising 2θ diffraction peak at about 5.87±0.2°, 6.42±0.2°, 10.11±0.2°, 12.58±0.2°, 13.38±0.2°, 16.12±0.2° and 17.86±0.2°. Preferably, the crystal form N of the pamoate of the compound of formula I has an XRPD pattern further comprising 2θ diffraction peak at about 10.55±0.2°, 14.74±0.2°, 24.90±0.2° and 26.45±0.2°. More preferably, the crystal form N of the pamoate of the compound of formula I has an XRPD pattern further comprising 2θ diffraction peak at about 10.87±0.2°, 23.55±0.2° and 24.29±0.2°.

In some embodiments, the crystal form N of the pamoate of the compound of formula I has an XRPD pattern comprising 2θ diffraction peak at about 5.87±0.2°, 6.42±0.2°, 10.11±0.2°, 10.55±0.2°, 12.58±0.2°, 13.38±0.2°, 14.74±0.2°, 16.12±0.2°, 17.86±0.2°, 24.90±0.2° and 26.45±0.2°. In other embodiments, the crystal form N of the pamoate of the compound of formula I has an XRPD pattern comprising 2θ diffraction peak at about 5.87±0.2°, 6.42±0.2°, 10.11±0.2°, 10.55±0.2°, 10.87±0.2°, 12.58±0.2°, 13.38±0.2°, 14.74±0.2°, 16.12±0.2°, 17.86±0.2°, 23.55±0.2°, 24.29±0.2°, 24.90±0.2°, and 26.45±0.2°.

In some embodiments, the crystal form N of the pamoate of the compound of formula I has an XRPD pattern comprising the following 2θ diffraction peak at:

| 2θ (°) ± 0.2° | intensity % |
|---|---|
| 5.87 | 50.69 |
| 6.42 | 20.09 |
| 9.01 | 8.73 |
| 10.11 | 29.52 |
| 10.55 | 60.03 |
| 10.87 | 46.88 |
| 11.23 | 15.05 |
| 11.84 | 11.28 |
| 12.58 | 32.03 |
| 13.00 | 7.95 |
| 13.38 | 100 |
| 14.27 | 11.17 |
| 14.74 | 75.86 |
| 15.62 | 18.67 |
| 16.12 | 37.95 |
| 16.89 | 14.69 |
| 17.16 | 19.02 |
| 17.86 | 33.61 |
| 18.43 | 52.59 |
| 19.04 | 10.16 |
| 19.59 | 19.52 |
| 19.87 | 16.22 |
| 20.31 | 19.93 |
| 20.97 | 8.99 |
| 21.47 | 16.32 |
| 22.22 | 37.25 |
| 22.62 | 24.95 |
| 22.84 | 20.56 |
| 23.01 | 17.03 |
| 23.55 | 15.02 |
| 24.00 | 6.47 |
| 24.29 | 20.66 |
| 24.90 | 20.21 |
| 25.13 | 18.31 |
| 25.40 | 15.34 |
| 25.56 | 11.56 |
| 26.11 | 7.31 |
| 26.45 | 12.56 |
| 26.94 | 6.63 |
| 27.35 | 10.52 |
| 28.04 | 3.34 |
| 28.80 | 11.74 |
| 29.54 | 2.18 |
| 30.01 | 5.7 |
| 30.50 | 4.29 |
| 31.68 | 5.48 |
| 32.17 | 2.79 |

Figure 14:
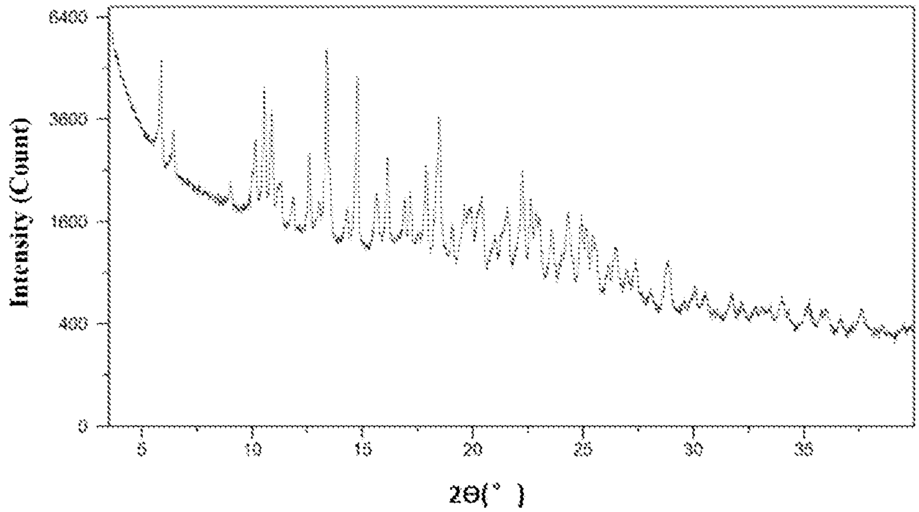
FIG. 14 shows the XRPD pattern of crystal form N of the pamoate of the compound of formula I.

In some embodiments, the crystal form N of the pamoate of the compound of formula I has an XRPD pattern substantially as shown in FIG. 14. In some preferred embodiments, the crystal form N of the pamoate of the compound of formula I has an XRPD pattern as shown in FIG. 14.

Crystal Form O

In some embodiments, provided is a crystal form O of the pamoate of the compound of formula I, wherein the stoichiometric ratio of the compound of formula I to pamoic acid is 2:1, and the crystal form O of the pamoate of the compound of formula I has an XRPD pattern comprising 2θ diffraction peak at about 11.33±0.2°, 11.92±0.2°, 14.71±0.2°, 16.11±0.2°, 17.50±0.2°, and 20.86±0.2°. Preferably, the crystal form O of the pamoate of the compound of formula I has an XRPD pattern further comprising 2θ diffraction peak at about 20.27±0.2°, 23.04±0.2°, 23.57±0.2° and 27.70±0.2°. More preferably, the crystal form O of the pamoate of the compound of formula I has an XRPD pattern further comprising 2θ diffraction peak at about 19.96±0.2°, 24.05±0.2°, 25.43±0.2° and 26.66±0.2°. In some embodiments, the crystal form O of the pamoate of the compound of formula I has an XRPD pattern comprising 2θ diffraction peak at about 11.33±0.2°, 11.92±0.2°, 14.71±0.2°, 16.11±0.2°, 17.50±0.2°, 20.27±0.2°, 20.86±0.2°, 23.04±0.2°, 23.57±0.2° and 27.70±0.2°. In other embodiments, the crystal form O of the pamoate of the compound of formula I has an XRPD pattern comprising 2θ diffraction peak at about 11.33±0.2°, 11.92±0.2°, 14.71±0.2°, 16.11±0.2°, 17.50±0.2°, 19.96±0.2°, 20.27±0.2°, 20.86±0.2°, 23.04±0.2°, 23.57±0.2°, 24.05±0.2°, 25.43±0.2°, 26.66±0.2°, and 27.70±0.2°.

In some embodiments, the crystal form O of the pamoate of the compound of formula I has an XRPD pattern comprising the following 2θ diffraction peak at

| 2θ (°) ± 0.2° | intensity % |
|---|---|
| 11.33 | 29.18 |
| 11.92 | 100 |
| 13.06 | 18.27 |
| 14.71 | 88.59 |
| 16.11 | 46.85 |
| 16.89 | 18.47 |
| 17.50 | 21.39 |
| 19.96 | 36.09 |
| 20.27 | 77.96 |
| 20.86 | 90.51 |
| 22.11 | 33.19 |
| 23.04 | 44.04 |
| 23.57 | 31.96 |
| 24.05 | 26.35 |
| 25.43 | 35.48 |
| 26.66 | 25.49 |
| 27.70 | 19.6 |
| 30.27 | 2.71 |
| 31.15 | 3.9 |
| 35.14 | 11.82 |
| 37.09 | 6.37 |

Figure 15:
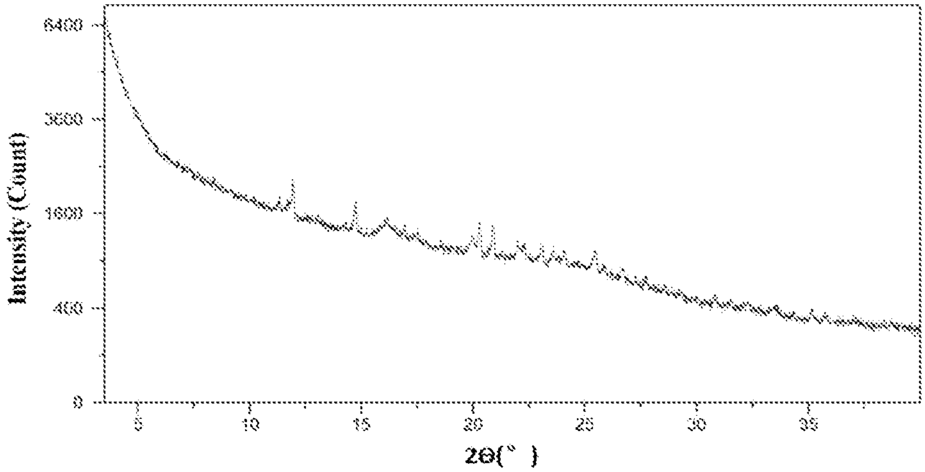
FIG. 15 shows the XRPD pattern of crystal form O of the pamoate of the compound of formula I.

In some embodiments, the crystal form O of the pamoate of the compound of formula I has an XRPD pattern substantially as shown in FIG. 15. In some preferred embodiments, the crystal form O of the pamoate of the compound of formula I has an XRPD pattern as shown in FIG. 15.

Crystal Form P

In some embodiments, provided is a crystal form P of the pamoate of the compound of formula I, wherein the stoichiometric ratio of the compound of formula I to pamoic acid is 2:1, and the crystal form P of the pamoate of the compound of formula I has an XRPD pattern comprising 2θ diffraction peak at about 5.79±0.2°, 6.36±0.2°, 10.58±0.2°, 10.90±0.2°, 13.32±0.2°, 14.69±0.2°, 17.61±0.2° and 25.26±0.2°.

Preferably, the crystal form P of the pamoate of the compound of formula I has an XRPD pattern further comprising 2θ diffraction peak at about 10.58±0.2°, 22.20±0.2°, 22.80±0.2° and 23.47±0.2°. More preferably, the crystal form P of the pamoate of the compound of formula I has an XRPD pattern further comprising 2θ diffraction peak at about 23.76±0.2° and 24.08±0.2°.

In some embodiments, the crystal form P of the pamoate of the compound of formula I has an XRPD pattern comprising 2θ diffraction peak at about 5.79±0.2°, 6.36±0.2°, 10.58±0.2°, 10.90±0.2°, 13.32±0.2°, 14.69±0.2°, 17.61±0.2°, 22.20±0.2°, 22.80±0.2°, 23.47±0.2° and 25.26±0.2°. In other embodiments, the crystal form P of the pamoate of the compound of formula I has an XRPD pattern comprising 2θ diffraction peak at about 5.79±0.2°, 6.36±0.2°, 10.58±0.2°, 10.90±0.2°, 13.32±0.2°, 14.69±0.2°, 17.61±0.2°, 22.20±0.2°, 22.80±0.2°, 23.47±0.2°, 23.76±0.2°, 24.08±0.2° and 25.26±0.2°.

In some embodiments, the crystal form P of the pamoate of the compound of formula I has an XRPD pattern comprising the following 2θ diffraction peak at:

| 2θ (°) ± 0.2° | intensity % |
|---|---|
| 5.79 | 57.05 |
| 6.36 | 19.21 |
| 8.81 | 9.5 |
| 10.15 | 33.3 |
| 10.58 | 100 |
| 10.90 | 41.33 |
| 11.17 | 19.56 |
| 11.70 | 5.26 |
| 12.50 | 35.98 |
| 13.19 | 40.76 |
| 13.32 | 89.16 |
| 14.44 | 29.3 |
| 14.69 | 55.55 |
| 15.61 | 15.55 |
| 15.90 | 18.97 |
| 16.72 | 29.29 |
| 16.97 | 21.7 |
| 17.38 | 5.71 |
| 17.61 | 47.83 |
| 18.33 | 56.34 |
| 18.71 | 20.03 |
| 18.93 | 16.22 |
| 19.50 | 19.06 |
| 19.77 | 28.99 |
| 19.89 | 42.23 |
| 20.03 | 42.73 |
| 20.34 | 15.28 |
| 20.48 | 11.04 |
| 21.28 | 37.18 |
| 21.94 | 17.28 |
| 22.20 | 67.88 |
| 22.80 | 22.45 |
| 22.99 | 22.64 |
| 23.47 | 18.42 |
| 23.76 | 21.59 |
| 24.08 | 32.62 |
| 24.51 | 9 |
| 24.70 | 12.85 |
| 24.94 | 13.61 |
| 25.26 | 32.75 |
| 26.37 | 24.71 |
| 27.13 | 9.44 |
| 27.60 | 3.09 |
| 28.31 | 15.42 |
| 28.79 | 6.66 |
| 29.35 | 3.9 |
| 29.99 | 5.89 |
| 30.27 | 3.94 |
| 30.98 | 3.82 |
| 31.67 | 4.42 |
| 32.36 | 8.72 |
| 33.35 | 12.85 |
| 33.89 | 2.14 |
| 35.31 | 5.04 |
| 35.62 | 3.72 |
| 36.03 | 4.64 |
| 36.47 | 3.34 |
| 37.50 | 3.5 |
| 39.37 | 1.45 |

Figure 16:
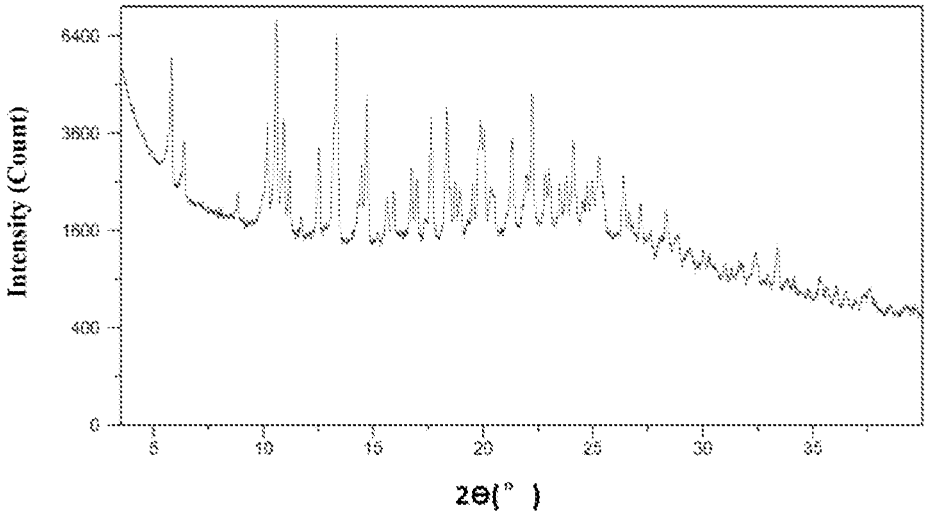
FIG. 16 shows the XRPD pattern of crystal form P of the pamoate of the compound of formula I.

In some embodiments, the crystal form P of the pamoate of the compound of formula I has an XRPD pattern substantially as shown in FIG. 16. In some preferred embodiments, the crystal form P of the pamoate of the compound of formula I has an XRPD pattern as shown in FIG. 16.

Crystal Form Q

In some embodiments, provided is a crystal form Q of the pamoate of the compound of formula I, wherein the stoichiometric ratio of the compound of formula I to pamoic acid is 2:1, and the crystal form Q of the pamoate of the compound of formula I has an XRPD pattern comprising 2θ diffraction peak at about 5.75±0.2°, 6.20±0.2°, 10.46±0.2°, 14.54±0.2°, 15.26±0.2°, and 20.78±0.2°. Preferably, the crystal form Q of the pamoate of the compound of formula I has an XRPD pattern further comprising 2θ diffraction peak at about 16.16±0.2°, 17.51±0.2° and 24.37±0.2°. More preferably, the crystal form Q of the pamoate of the compound of formula I has an XRPD pattern further comprising 2θ diffraction peak at about 17.98±0.2°, 21.74±0.2° and 23.58±0.2°.

In some embodiments, the crystal form Q of the pamoate of the compound of formula I has an XRPD pattern comprising 2θ diffraction peak at about 5.75±0.2°, 6.20±0.2°, 10.46±0.2°, 14.54±0.2°, 15.26±0.2°, 16.16±0.2°, 17.51±0.2°, 20.78±0.2° and 24.37±0.2°. In other embodiments, the crystal form Q of the pamoate of the compound of formula I has an XRPD pattern comprising 2θ diffraction peak at about 5.75±0.2°, 6.20±0.2°, 10.46±0.2°, 14.54±0.2°, 15.26±0.2°, 16.16±0.2°, 17.51±0.2°, 17.98±0.2°, 20.78±0.2°, 21.74±0.2°, 23.58±0.2° and 24.37±0.2°.

In some embodiments, the crystal form Q of the pamoate of the compound of formula I has an XRPD pattern comprising the following 2θ diffraction peak at:

| 2θ (°) ± 0.2° | intensity % |
|---|---|
| 5.75 | 52.33 |
| 6.20 | 11.39 |
| 9.01 | 9.55 |
| 10.10 | 41.7 |
| 10.46 | 35.54 |
| 10.70 | 39.6 |
| 10.89 | 27.15 |
| 11.62 | 14.35 |
| 12.57 | 35.96 |
| 13.17 | 79.31 |
| 13.55 | 16.8 |
| 13.97 | 8.13 |
| 14.54 | 100 |
| 15.26 | 22.97 |
| 16.16 | 32.13 |
| 16.92 | 27.26 |
| 17.51 | 18.44 |
| 17.98 | 44.48 |
| 18.51 | 24.34 |
| 18.99 | 23.67 |
| 19.61 | 34.85 |
| 19.77 | 29.48 |
| 20.27 | 12.22 |
| 20.78 | 20.93 |
| 21.36 | 38.07 |
| 21.74 | 23.23 |
| 22.23 | 38.68 |
| 22.69 | 25.38 |
| 23.58 | 45.14 |
| 24.37 | 26.69 |
| 25.01 | 7.82 |
| 25.41 | 7.63 |
| 26.21 | 6.45 |
| 27.32 | 5.21 |
| 28.16 | 8.34 |
| 28.86 | 8.63 |
| 29.39 | 6.63 |
| 30.25 | 7.26 |
| 31.62 | 3.25 |
| 33.15 | 9.86 |
| 33.97 | 5.37 |
| 34.62 | 5.62 |
| 35.65 | 9.97 |
| 37.28 | 4.73 |

Figure 17:
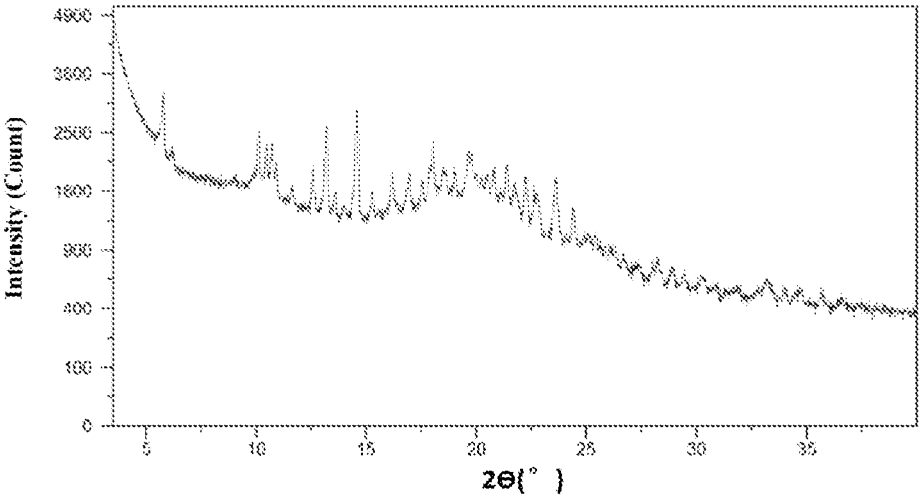
FIG. 17 shows the XRPD pattern of crystal form Q of the pamoate of the compound of formula I.

In some embodiments, the crystal form Q of the pamoate of the compound of formula I has an XRPD pattern substantially as shown in FIG. 17. In some preferred embodiments, the crystal form Q of the pamoate of the compound of formula I has an XRPD pattern as shown in FIG. 17.

Crystal Form R

In some embodiments, provided is a crystal form R of the pamoate of the compound of formula I, wherein the stoichiometric ratio of the compound of formula I to pamoic acid is 2:1, and the crystal form R of the pamoate of the compound of formula I has an XRPD pattern comprising 2θ diffraction peak at about 5.97±0.2°, 11.45±0.2°, 12.06±0.2°, 13.41±0.2°, 17.75±0.2°, and 18.77±0.2°. Preferably, the crystal form R of the pamoate of the compound of formula I has an XRPD pattern further comprising 2θ diffraction peak at about 19.42±0.2°, 21.64±0.2°, 23.89±0.2°, 27.10±0.2° and 28.76±0.2°. More preferably, the crystal form R of the pamoate of the compound of formula I has an XRPD pattern further comprising 2θ diffraction peak at about 21.64±0.2°, 23.09±0.2° and 26.18±0.2°.

In some embodiments, the crystal form R of the pamoate of the compound of formula I has an XRPD pattern comprising 2θ diffraction peak at about 5.97±0.2°, 11.45±0.2°, 12.06±0.2°, 13.41±0.2°, 17.75±0.2°, 18.77±0.2°, 19.42±0.2°, 21.64±0.2°, 23.89±0.2°, 27.10±0.2° and 28.76±0.2°. In other embodiments, the crystal form R of the pamoate of the compound of formula I has an XRPD pattern comprising 2θ diffraction peak at about 5.97±0.2°, 11.45±0.2°, 12.06±0.2°, 13.41±0.2°, 17.75±0.2°, 18.77±0.2°, 19.42±0.2°, 21.64±0.2°, 23.09±0.2°, 23.89±0.2°, 26.18±0.2°, 27.10±0.2° and 28.76±0.2°.

In some embodiments, the crystal form R of the pamoate of the compound of formula I has an XRPD pattern comprising the following 2θ diffraction peak at:

| 2θ (°) ± 0.2° | intensity % |
|---|---|
| 5.97 | 53.51 |
| 10.90 | 39.56 |
| 11.45 | 44.85 |
| 12.06 | 10.04 |
| 12.31 | 22.51 |
| 13.41 | 39.96 |
| 14.72 | 34.38 |
| 16.18 | 14.59 |
| 17.05 | 2.88 |
| 17.75 | 100 |
| 18.77 | 55.22 |
| 19.11 | 16.93 |
| 19.42 | 20.99 |
| 20.36 | 16.55 |
| 21.19 | 41.66 |
| 21.64 | 48.3 |
| 21.98 | 8.55 |
| 22.32 | 33.93 |
| 23.09 | 73.04 |
| 23.49 | 21 |
| 23.89 | 55.03 |
| 24.80 | 15.13 |
| 26.18 | 10.23 |
| 26.66 | 6.3 |
| 27.10 | 15.42 |
| 27.67 | 8.06 |
| 28.39 | 1.7 |
| 28.76 | 10.66 |
| 29.33 | 6.53 |
| 29.87 | 4.11 |
| 30.51 | 10.55 |
| 30.85 | 2.08 |
| 31.28 | 11.28 |
| 32.16 | 7.67 |
| 32.74 | 2.1 |
| 33.12 | 2.07 |
| 34.30 | 10.26 |
| 35.41 | 4.58 |
| 35.79 | 5.09 |
| 36.69 | 4.75 |
| 36.87 | 3.48 |
| 37.97 | 7.65 |
| 39.63 | 1.37 |

-continued

Figure 18:
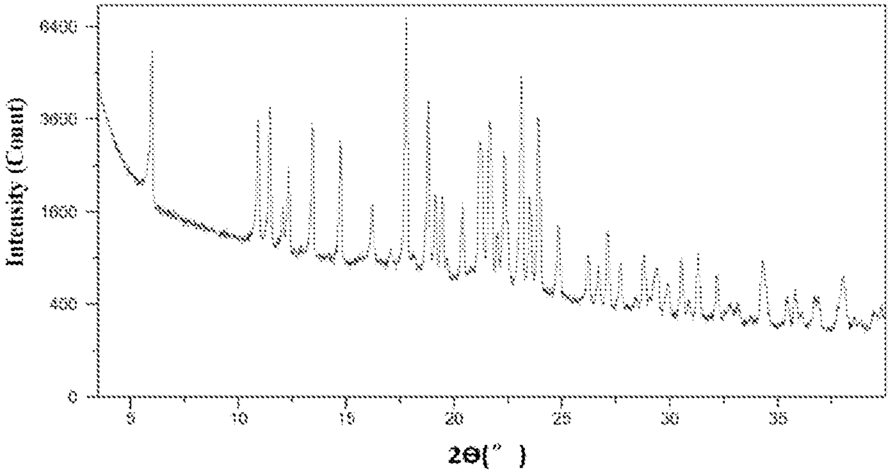
FIG. 18 shows the XRPD pattern of crystal form R of the pamoate of the compound of formula I.

In some embodiments, the crystal form R of the pamoate of the compound of formula I has an XRPD pattern substantially as shown in FIG. 18. In some preferred embodiments, the crystal form R of the pamoate of the compound of formula I has an XRPD pattern as shown in FIG. 18.

Crystal Form S

In some embodiments, provided is a crystal form S of the pamoate of the compound of formula I, wherein the stoichiometric ratio of the compound of formula I to pamoic acid is 2:1, and the crystal form S of the pamoate of the compound of formula I has an XRPD pattern comprising 2θ diffraction peak at about 5.84±0.2°, 6.34±0.2°, 10.06±0.2°, 11.14±0.2°, 13.25±0.2°, 14.65±0.2°, 18.26±0.2° and 25.25±0.2°. Preferably, the crystal form S of the pamoate of the compound of formula I has an XRPD pattern further comprising 2θ diffraction peak at about 19.33±0.2°, 21.53±0.2°, 22.68±0.2° and 24.06±0.2°. More preferably, the crystal form S of the pamoate of the compound of formula I has an XRPD pattern further comprising 2θ diffraction peak at about 20.20±0.2°, 22.09±0.2° and 24.06±0.2°.

In some embodiments, the crystal form S of the pamoate of the compound of formula I has an XRPD pattern comprising 2θ diffraction peak at about 5.84±0.2°, 6.34±0.2°, 10.06±0.2°, 11.14±0.2°, 13.25±0.2°, 14.65±0.2°, 18.26±0.2°, 19.33±0.2°, 21.53±0.2°, 22.68±0.2°, 24.06±0.2° and 25.25±0.2°. In other embodiments, the crystal form S of the pamoate of the compound of formula I has an XRPD pattern comprising 2θ diffraction peak at about 5.84±0.2°, 6.34±0.2°, 10.06±0.2°, 11.14±0.2°, 13.25±0.2°, 14.65±0.2°, 18.26±0.2°, 19.33±0.2°, 20.20±0.2°, 21.53±0.2°, 22.09±0.2°, 22.68±0.2°, 24.06±0.2°, and 25.25±0.2°.

In some embodiments, the crystal form S of the pamoate of the compound of formula I has an XRPD pattern comprising the following 2θ diffraction peak at:

| 2θ (°) ± 0.2° | intensity % |
|---|---|
| 5.84 | 40.37 |
| 6.34 | 13.66 |
| 10.06 | 38.13 |
| 10.44 | 56.63 |
| 10.73 | 42.12 |
| 11.14 | 31.27 |
| 11.79 | 11.98 |
| 12.55 | 34.85 |
| 13.25 | 93.16 |
| 13.57 | 16.21 |
| 14.11 | 14.28 |
| 14.65 | 100 |
| 15.47 | 24.51 |
| 16.14 | 34.05 |
| 17.06 | 18.77 |
| 17.84 | 24.89 |
| 18.26 | 63.88 |
| 18.85 | 11.15 |
| 19.33 | 20.1 |
| 19.66 | 31.74 |
| 20.20 | 40.65 |
| 20.49 | 16.8 |
| 21.11 | 21.74 |
| 21.53 | 33.74 |

-continued

| 2θ (°) ± 0.2° | intensity % |
|---|---|
| 22.09 | 45.98 |
| 22.68 | 46.47 |
| 23.48 | 17.16 |
| 24.06 | 24.52 |
| 24.60 | 22.74 |
| 25.25 | 21.3 |
| 26.24 | 16.84 |
| 26.78 | 13.11 |
| 27.37 | 13.17 |
| 27.80 | 7.58 |
| 28.60 | 12.51 |
| 30.16 | 6.99 |
| 31.76 | 3.59 |
| 33.28 | 5.8 |
| 34.03 | 5.91 |
| 34.87 | 6.41 |
| 35.60 | 4.62 |
| 37.34 | 3.84 |

Figure 19:
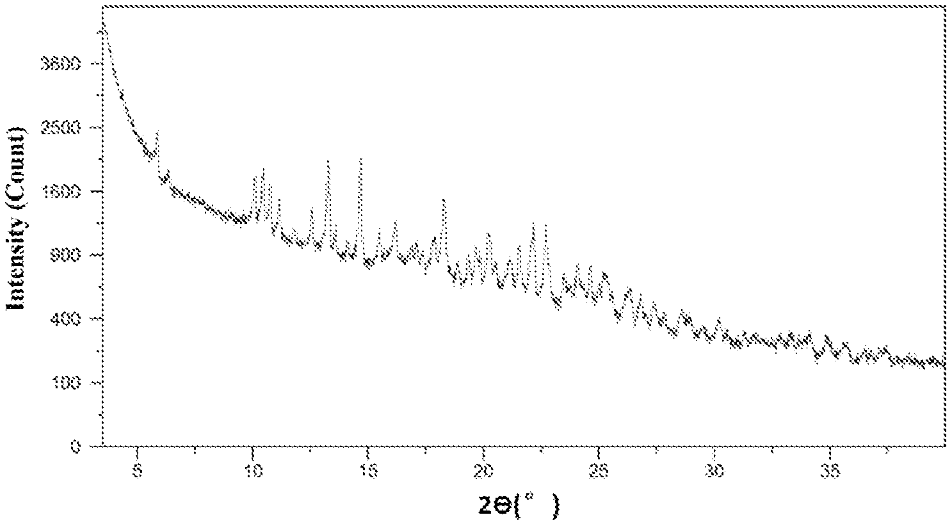
FIG. 19 shows the XRPD pattern of crystal form S of the pamoate of the compound of formula I.

In some embodiments, the crystal form S of the pamoate of the compound of formula I has an XRPD pattern substantially as shown in FIG. 19. In some preferred embodiments, the crystal form S of the pamoate of the compound of formula I has an XRPD pattern as shown in FIG. 19.

Palmitate of the Compound of Formula I and Crystal Form Thereof (1:1)

In some embodiments, the stoichiometric ratio of the compound of formula I to palmitic acid in the palmitate of the compound of formula I is 1:1.

Crystal Form T

In some embodiments, provided is a crystal form T of the palmitate of the compound of formula I, wherein the stoichiometric ratio of the compound of formula I to palmitic acid is 1:1, and the crystal form T of the palmitate of the compound of formula I has an XRPD pattern comprising 2θ diffraction peak at about 6.17±0.2°, 9.73±0.2°, 10.20±0.2°, 11.52±0.2°, 12.44±0.2°, 15.16±0.2° and 21.40±0.2°. Preferably, the crystal form T of the palmitate of the compound of formula I has an XRPD pattern further comprising 2θ diffraction peak at about 13.82±0.2°, 16.36±0.2° and 16.65±0.2°. More preferably, the crystal form T of the palmitate of the compound of formula I has an XRPD pattern further comprising 2θ diffraction peak at about 16.89±0.2°, 19.88±0.2° and 20.18±0.2°.

In some embodiments, the crystal form T of the palmitate of the compound of formula I has an XRPD pattern comprising 2θ diffraction peak at about 6.17±0.2°, 9.73±0.2°, 10.20±0.2°, 11.52±0.2°, 12.44±0.2°, 13.82±0.2°, 15.16±0.2°, 16.36±0.2°, 16.65±0.2° and 21.40±0.2°. In other embodiments, the crystal form T of the palmitate of the compound of formula I has an XRPD pattern comprising 2θ diffraction peak at about 6.17±0.2°, 9.73±0.2°, 10.20±0.2°, 11.52±0.2°, 12.44±0.2°, 13.82±0.2°, 15.16±0.2°, 16.36±0.2°, 16.65±0.2°, 16.89±0.2°, 19.88±0.2°, 20.18±0.2° and 21.40±0.2°.

In some embodiments, the crystal form T of the palmitate of the compound of formula I has an XRPD pattern comprising the following 2θ diffraction peak at:

| 2θ (°) ± 0.2° | intensity % |
|---|---|
| 6.17 | 100 |
| 7.49 | 0.69 |
| 9.73 | 7.35 |
| 10.20 | 9.57 |

-continued

| 2θ (°) ± 0.2° | intensity % |
|---|---|
| 11.52 | 5.48 |
| 12.44 | 11.53 |
| 13.15 | 2.62 |
| 13.82 | 12.67 |
| 14.19 | 6.2 |
| 14.54 | 1.46 |
| 15.16 | 24.44 |
| 16.36 | 10.22 |
| 16.65 | 12 |
| 16.89 | 11.65 |
| 17.91 | 1.69 |
| 18.74 | 5.62 |
| 19.29 | 4.53 |
| 19.59 | 5.81 |
| 19.88 | 57.7 |
| 20.18 | 36.92 |
| 20.57 | 6.92 |
| 21.40 | 98.19 |
| 21.85 | 2.31 |
| 22.29 | 1.25 |
| 22.88 | 7.68 |
| 23.25 | 3.61 |
| 23.67 | 0.7 |
| 24.09 | 2.75 |
| 24.30 | 2.13 |
| 24.79 | 2.39 |
| 25.34 | 2.78 |
| 25.83 | 4.84 |
| 26.29 | 4.1 |
| 26.64 | 3.26 |
| 27.11 | 1.67 |
| 28.01 | 0.87 |
| 28.37 | 1.3 |
| 28.72 | 4.32 |
| 29.71 | 1.11 |
| 30.21 | 0.42 |
| 30.64 | 1.48 |
| 31.25 | 1.81 |
| 31.64 | 2.25 |
| 32.01 | 1.19 |
| 32.34 | 1.61 |
| 33.11 | 0.84 |
| 33.53 | 0.96 |

Figure 20:
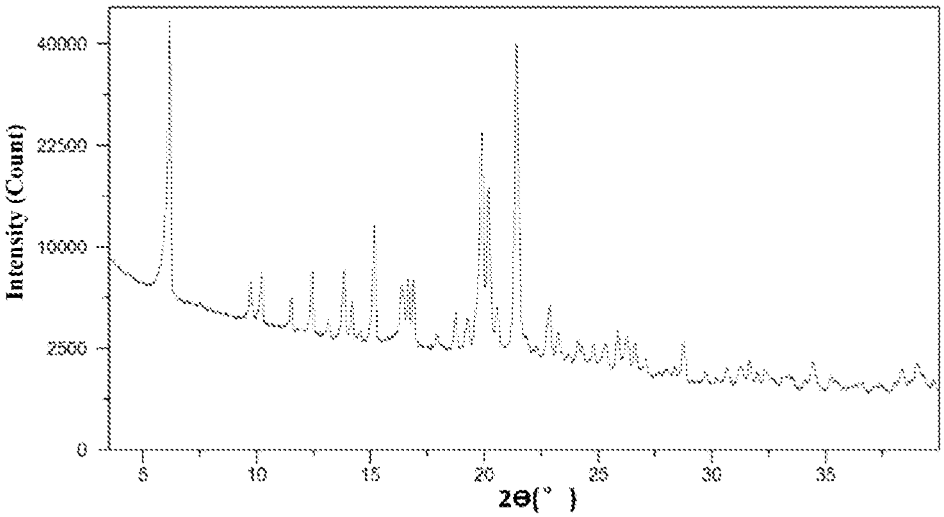
FIG. 20 shows the XRPD pattern of crystal form T of the palmitate of the compound of formula I.

In some embodiments, the crystal form T of the palmitate of the compound of formula I has an XRPD pattern substantially as shown in FIG. 20. In some preferred embodiments, the crystal form T of the palmitate of the compound of formula I has an XRPD pattern as shown in FIG. 20.

Crystal Form U

In some embodiments, provided is a crystal form U of the palmitate of the compound of formula I, wherein the stoichiometric ratio of the compound of formula I to palmitic acid is 1:1, and the crystal form U of the palmitate of the compound of formula I has an XRPD pattern comprising 2θ diffraction peak at about 5.95±0.2°, 15.15±0.2°, 17.90±0.2°, 20.57±0.2°, 21.44±0.2°, 21.83±0.2° and 25.82±0.2°. Preferably, the crystal form U of the palmitate of the compound of formula I has an XRPD pattern further comprising 2θ diffraction peak at about 10.81±0.2°, 14.47±0.2°, 18.20±0.2°, 22.63±0.2° and 26.63±0.2°. More preferably, the crystal form U of the palmitate of the compound of formula I has an XRPD pattern further comprising 2θ diffraction peak at about 11.27±0.2° and 26.03±0.2°.

In some embodiments, the crystal form U of the palmitate of the compound of formula I has an XRPD pattern comprising 2θ diffraction peak at about 5.95±0.2°, 10.81±0.2°, 14.47±0.2°, 15.15±0.2°, 17.90±0.2°, 18.20±0.2°, 20.57±0.2°, 21.44±0.2°, 21.83±0.2°, 22.63±0.2°, 25.82±0.2° and 26.63±0.2°. In other embodiments, the crystal form U of the palmitate of the compound of formula I has an XRPD pattern comprising 2θ diffraction peak at about 5.95±0.2°, 10.81±0.2°, 11.27±0.2°, 14.47±0.2°, 15.15±0.2°, 17.90±0.2°, 18.20±0.2°, 20.57±0.2°, 21.44±0.2°, 21.83±0.2°, 22.63±0.2°, 25.82±0.2°, 26.03±0.2°, and 26.63±0.2°.

In some embodiments, the crystal form U of the palmitate of the compound of formula I has an XRPD pattern comprising the following 2θ diffraction peak at:

| 2θ (°) ± 0.2° | intensity % |
|---|---|
| 4.86 | 0.85 |
| 5.95 | 14.7 |
| 7.33 | 1.93 |
| 10.81 | 3.42 |
| 11.27 | 2.28 |
| 13.31 | 0.54 |
| 14.02 | 0.67 |
| 14.47 | 2.86 |
| 15.15 | 10.28 |
| 15.43 | 1.02 |
| 16.39 | 5.45 |
| 17.90 | 21.16 |
| 18.20 | 9.45 |
| 18.34 | 4.48 |
| 18.59 | 5.16 |
| 18.98 | 3.2 |
| 19.26 | 1.54 |
| 19.51 | 1.96 |
| 19.89 | 2.45 |
| 20.02 | 3.29 |
| 20.25 | 6.64 |
| 20.57 | 24.68 |
| 21.44 | 100 |
| 21.83 | 31.75 |
| 22.24 | 2.74 |
| 22.63 | 5.71 |
| 22.78 | 5.69 |
| 23.24 | 5.44 |
| 23.68 | 1.78 |
| 24.00 | 9.24 |
| 24.83 | 0.31 |
| 25.32 | 0.89 |
| 25.82 | 13.02 |
| 26.03 | 14.48 |
| 26.46 | 3.12 |
| 26.63 | 4.05 |
| 27.01 | 1.43 |
| 27.53 | 1.17 |
| 28.85 | 0.66 |
| 29.09 | 0.94 |

Figure 21:
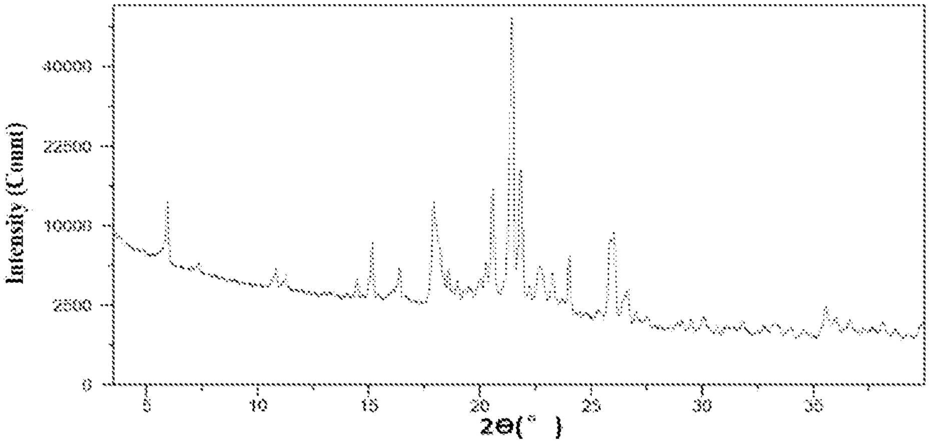
FIG. 21 shows the XRPD pattern of crystal form U of the palmitate of the compound of formula I.

In some embodiments, the crystal form U of the palmitate of the compound of formula I has an XRPD pattern substantially as shown in FIG. 21. In some preferred embodiments, the crystal form U of the palmitate of the compound of formula I has an XRPD pattern as shown in FIG. 21.

Crystal Form V

In some embodiments, provided is a crystal form V of the palmitate of the compound of formula I, wherein the stoichiometric ratio of the compound of formula I to palmitic acid is 1:1, and the crystal form V of the palmitate of the compound of formula I has an XRPD pattern comprising 2θ diffraction peak at about 5.56±0.2°, 12.99±0.2°, 13.21±0.2°, 13.59±0.2°, 14.02±0.2°, 14.71±0.2° and 19.90±0.2°. Preferably, the crystal form V of the palmitate of the compound of formula I has an XRPD pattern further comprising 2θ diffraction peak at about 11.19±0.2°, 19.66±0.2°, 22.61±0.2°, 22.80±0.2° and 23.43±0.2°. More preferably, the crystal form V of the palmitate of the compound of formula I has an XRPD pattern further comprising 2θ diffraction peak at about 11.38±0.2°, 19.48±0.2°, 20.26±0.2° and 22.96±0.2°.

In some embodiments, the crystal form V of the palmitate of the compound of formula I has an XRPD pattern comprising 2θ diffraction peak at about 5.56±0.2°, 11.19±0.2°, 12.99±0.2°, 13.21±0.2°, 13.59±0.2°, 14.02±0.2°, 14.71±0.2°, 19.90±0.2°, 19.66±0.2°, 22.61±0.2°, 22.80±0.2° and 23.43±0.2°. In other embodiments, the crystal form V of the palmitate of the compound of formula I has an XRPD pattern comprising 2θ diffraction peak at about 5.56±0.2°, 11.19±0.2°, 11.38±0.2°, 12.99±0.2°, 13.21±0.2°, 13.59±0.2°, 14.02±0.2°, 14.71±0.2°, 19.48±0.2°, 19.90±0.2°, 19.66±0.2°, 20.26±0.2°, 22.61±0.2°, 22.80±0.2°, 22.96±0.2° and 23.43±0.2°.

In some embodiments, the crystal form V of the palmitate of the compound of formula I has an XRPD pattern comprising the following 2θ diffraction peak at:

| 2θ (°) ± 0.2° | intensity % |
|---|---|
| 5.56 | 11.79 |
| 6.40 | 1.29 |
| 6.98 | 1.04 |
| 7.64 | 0.7 |
| 8.40 | 0.93 |
| 10.32 | 0.64 |
| 11.19 | 14.05 |
| 11.38 | 13.48 |
| 11.64 | 9.04 |
| 12.05 | 3.26 |
| 12.59 | 2.55 |
| 12.99 | 10.58 |
| 13.21 | 9.65 |
| 13.31 | 7.82 |
| 13.59 | 12.39 |
| 14.02 | 25.5 |
| 14.71 | 17.85 |
| 14.99 | 10.8 |
| 15.43 | 14.53 |
| 15.95 | 12 |
| 16.26 | 18.36 |
| 16.86 | 10.39 |
| 17.14 | 10.55 |
| 18.11 | 10.37 |
| 18.61 | 1.34 |
| 19.13 | 5.89 |
| 19.48 | 53.74 |
| 19.66 | 40.27 |
| 19.90 | 71.68 |
| 20.26 | 19.18 |
| 20.71 | 2.76 |
| 21.04 | 3.23 |
| 21.30 | 1.97 |
| 21.82 | 0.86 |
| 22.61 | 78.44 |
| 22.80 | 100 |
| 22.96 | 49.25 |
| 23.43 | 54.37 |
| 23.78 | 27.3 |
| 24.06 | 7.03 |

Figure 22:
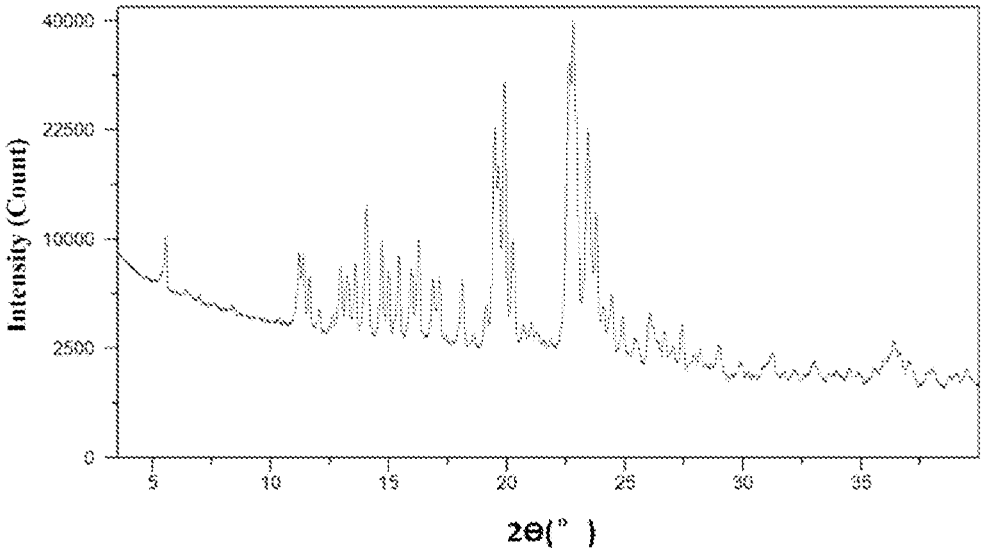
FIG. 22 shows the XRPD pattern of crystal form V of the palmitate of the compound of formula I.

In some embodiments, the crystal form V of the palmitate of the compound of formula I has an XRPD pattern substantially as shown in FIG. 22. In some preferred embodiments, the crystal form V of the palmitate of the compound of formula I has an XRPD pattern as shown in FIG. 22.

Pharmaceutical Compositions and Uses

Another purpose of present disclosure is to provide a pharmaceutical composition comprising a salt of the compound of formula I, wherein the salt is selected from the group consisting of pamoate and palmitate, and particularly a crystal form of the pamoate or a crystal form of the palmitate of the compound of formula I, and one or more pharmaceutically acceptable carriers.

Another purpose of present disclosure is to provide use of a salt of the compound of formula I of present disclosure (such as a pamoate of the compound of formula I and a palmitate of the compound of formula I, especially a crystal form of the pamoate or a crystal form of the palmitate of the compound of formula I or any combination thereof) or a pharmaceutical composition in the manufacture of a medicament for the treatment of Parkinson's disease and restless leg syndrome.

Another purpose of present disclosure is to provide a salt of the compound of formula I of present disclosure (such as a pamoate of the compound of formula I and a palmitate of the compound of formula I, especially a crystal form of the pamoate or a crystal form of the palmitate of the compound of formula I or any combination thereof) or a pharmaceutical composition for the treatment of Parkinson's disease and restless leg syndrome.

Another purpose of present disclosure is to provide a method for treating Parkinson's disease and restless leg syndrome, comprising administering a therapeutically effective amount of a salt of the compound of formula I of present disclosure (such as a pamoate of the compound of formula I and a palmitate of the compound of formula I, especially a crystal form of the pamoate or a crystal form of the palmitate of the compound of formula I or any combination thereof) or a pharmaceutical composition to a subject in need thereof.

The term "pharmaceutically acceptable carrier" used herein refers to a diluent, adjuvant, excipient or vehicle with which a therapeutic agent is administered, and within the scope of reasonable medical judgement, it is suitable for contacting human and/or other animal tissues without excessive toxicity, irritation, allergic reaction or other problems or complications corresponding to reasonable benefit/risk ratio.

The administration of a compound of present disclosure in a pure form or in a suitable pharmaceutical composition may be carried out by providing any acceptable mode of administration of a medicament for similar use. The pharmaceutical composition of present disclosure can be prepared by combining the compound of present disclosure or salt thereof with a suitable pharmaceutically acceptable carrier.

The pharmaceutical composition of present disclosure can be manufactured by a method well-known in the art, such as conventional mixing method, etc.

Typical routes of administration of the compound of present disclosure or pharmaceutical composition thereof include but not limited to oral, rectal, transmucosal, intestinal administration, or local, percutaneous, inhalation, parenteral, sublingual, vaginal, nasal, intraocular, intraperitoneal, intramuscular, subcutaneous, and intravenous administration.

In a preferred embodiment, the pharmaceutical composition is in an oral form. For oral administration, the pharmaceutical composition can be prepared by mixing the active compound with a pharmaceutically acceptable carrier, excipient and/or medium that is well known in the art. These carriers, excipients and media can enable the compounds of the disclosure to be prepared as tablets, pills, lozenges, sugar coating agents, capsules, liquids, gel, slurries, suspensions, etc., which are used for oral administration to patients.

The solid oral composition can be prepared by conventional mixing, filling or tablet pressing methods. For example, it can be obtained by the following method: mixing the active compound with the solid excipient, optionally grinding the resulting mixture, adding other suitable auxiliary agents if necessary, and then processing the mixture into granules to obtain the core of tablets or sugar coating agents.

Beneficial Effects

The pamoate and palmitate of the compound of formula I of present disclosure have the advantages of high purity, good stability, etc. In addition, pamoate and palmitate of the compound of formula I of present disclosure have lower solubility and can be used for long-acting sustained release formulations. The pamoate and palmitate of the compound of formula I of present disclosure have extended $T_{max}$ and $T_{1/2}$ duration, which can maintain the effective blood concentration for a longer time, thereby thus proving that they can achieve the effect of long-acting release.

The crystal forms of present disclosure (such as crystal forms A-S and T-V) have the advantages of high purity, good stability, etc. In addition, the crystal forms of present disclosure have lower solubility and can be used for long-acting sustained release formulations. The crystal forms of present disclosure have extended $T_{max}$ and $T_{1/2}$ duration, which can maintain the effective blood concentration for a longer time, thereby proving that they can achieve the effect of long-acting release.

EXAMPLES

X-Ray Powder Diffraction (XRPD):

XRPD pattern of each crystal were collected by X'Pert3 Powder powder diffractometer. The instrument was irradiated by Cu Pd, and continuous projection scanning was carried out by Absolute scan at room temperature, and the range of scanning 2θ was from 3.5° to 40°, the step length was 0.013°, the dwell time was 50 s, and the scanning was conducted once.

All solvents used in present disclosure are commercially available and can be used without further purification.

Example 1: Preparation of Crystal Form a of the Pamoate of the Compound of Formula I 50 mg of compound of formula I and 92 mg of pamoic acid were taken into 2 mL of methanol, and placed in an environment of 40-10° C. cyclic heating and cooling (40-10° C. cyclic heating and cooling means that the temperature was maintained at 40° C. for 1 h, then dropped to 10° C. and maintained for 1 h, and then raised to 40° C. and maintained for 1 h, then dropped to 10° C. and maintained for 1 h, and repeated for cycles) to be suspended by vibration for 24 hours, and then centrifuged to obtain crystal form A of the pamoate of the compound of formula I, which was detected by XRPD. The XRPD pattern obtained is shown in FIG. 1.

Example 2: Preparation of Crystal Form B of the Pamoate of the Compound of Formula I 50 mg of the compound of formula I and 92 mg of pamoic acid were taken into 2 mL of acetonitrile, and placed in an environment of 40-10° C. cyclic heating and cooling to be suspended by vibration for 24 hours, and then centrifuged to obtain crystal form B of the pamoate of the compound of formula I, which was detected by XRPD. The XRPD pattern obtained is shown in FIG. 2.

Example 3: Preparation of Crystal Form C of the Pamoate of the Compound of Formula I 50 mg of the compound of formula I and 92 mg of pamoic acid were taken into 2 mL of acetone, and placed in an environment of 40-10° C. cyclic heating and cooling to be suspended by vibration for 24 hours, and then centrifuged to obtain crystal form C of the pamoate of the compound of formula I, which was detected by XRPD. The XRPD pattern obtained is shown in FIG. 3.

Example 4: Preparation of Crystal Form D of the Pamoate of the Compound of Formula I 50 mg of the compound of formula I and 92 mg of pamoic acid were taken into 2 mL of methanol, and placed in an environment of 40-10° C. cyclic heating and cooling to be suspended by vibration for 24 hours, and then centrifuged, and then dried at 60° C. to obtain crystal form D of the pamoate of the compound of formula I, which was detected by XRPD. The XRPD pattern obtained is shown in FIG. 4.

Example 5: Preparation of Crystal Form E of the Pamoate of the Compound of Formula I 50 mg of the compound of formula I and 92 mg of pamoic acid were taken into a mixed solvent of 1 mL of acetonitrile and 1 mL of water, and placed in an environment of 40-10° C. cyclic heating and cooling to be suspended by vibration for 24 hours, and then centrifuged to obtain crystal form E of the pamoate of the compound of formula I, which was detected by XRPD. The XRPD pattern obtained is shown in FIG. 5.

Example 6: Preparation of Crystal Form F of the Pamoate of the Compound of Formula I 50 mg of the compound of formula I and 92 mg of pamoic acid were taken into 3 mL of acetonitrile, and placed in an environment of 40-10° C. cyclic heating and cooling to be suspended by vibration for 24 hours, and then centrifuged, and then dried at 60° C. to obtain crystal form F of the pamoate of the compound of formula I, which was detected by XRPD. The XRPD pattern obtained is shown in FIG. 6.

Example 7: Preparation of Crystal Form G of the Pamoate of the Compound of Formula I 50 mg of the compound of formula I and 92 mg of pamoic acid were taken into 4 mL of acetonitrile, and placed in an environment of 50° C. to be suspended by vibration for 4 hours, and then centrifuged to obtain crystal form G of the pamoate of the compound of formula I, which was detected by XRPD. The XRPD pattern obtained is shown in FIG. 7.

Example 8: Preparation of Crystal Form H of the Pamoate of the Compound of Formula I 50 mg of the compound of formula I and 92 mg of pamoic acid were taken into 4 mL of methanol, and placed in an environment of 50° C. to be suspended by vibration for 4 hours, and then centrifuged to obtain crystal form H of the pamoate of the compound of formula I, which was detected by XRPD. The XRPD pattern obtained is shown in FIG. 8.

Example 9: Preparation of Crystal Form I of the Pamoate of the Compound of Formula I 50 mg of the compound of formula I and 92 mg of pamoic acid were taken into a mixed solvent of 1 mL of methanol and 1 mL of water, and placed in an environment of 25° C. to be suspended by vibration for 24 hours, and then centrifuged to obtain crystal form I of the pamoate of the compound of formula I, which was detected by XRPD. The XRPD pattern obtained is shown in FIG. 9.

Example 10: Preparation of Crystal Form J of the Pamoate of the Compound of Formula I 50 mg of the compound of formula I and 92 mg of pamoic acid were taken into 2 mL of THF, and placed in an environment of 40-10° C. cyclic heating and cooling to be suspended by vibration for 24 hours, and then centrifuged to obtain crystal form J of the pamoate of the compound of formula I, which was detected by XRPD. The XRPD pattern obtained is shown in FIG. 10.

Example 11: Preparation of Crystal Form K of the Pamoate of the Compound of Formula I 50 mg of the compound of formula I and 92 mg of pamoic acid were taken into a mixed solution of 1 mL of methanol and 3 mL of water, and placed in an environment of 40-10° C. cyclic heating and cooling to be suspended by vibration for 24 hours, and then centrifuged to obtain crystal form K of the pamoate of the compound of formula I, which was detected by XRPD. The XRPD pattern obtained is shown in FIG. 11.

Example 12: Preparation of Crystal Form L of the Pamoate of the Compound of Formula I 50 mg of the compound of formula I and 92 mg of pamoic acid were taken into a mixed solution of 0.4 mL of methanol and 1.6 mL of MTBE, and placed in an environment of 40-10° C. cyclic heating and cooling to be suspended by vibration for 24 hours, and then centrifuged to obtain crystal form L of the pamoate of the compound of formula I, which was detected by XRPD. The XRPD pattern obtained is shown in FIG. 12.

Example 13: Preparation of Crystal Form M of the Pamoate of the Compound of Formula I 50 mg of the compound of formula I and 92 mg of pamoic acid were taken into a mixed solution of 1 mL of THE and 1 mL of water, and placed in an environment of 40-10° C. cyclic heating and cooling to be suspended by vibration for 24 hours, and then centrifuged to obtain crystal form M of the pamoate of the compound of formula I, which was detected by XRPD. The XRPD pattern obtained is shown in FIG. 13.

Example 14: Preparation of Crystal Form N of the Pamoate of the Compound of Formula I 50 mg of the compound of formula I and 46 mg of pamoic acid were taken into 2 mL of acetone, and placed in an environment of 40-10° C. cyclic heating and cooling to be suspended by vibration for 24 hours, and then centrifuged to obtain crystal form N of the pamoate of the compound of formula I, which was detected by XRPD. The XRPD pattern obtained is shown in FIG. 14.

Example 15: Preparation of Crystal Form O of the Pamoate of the Compound of Formula I 50 mg of the compound of formula I and 46 mg of pamoic acid were taken into 2 mL of methanol, and placed in an environment of 40-10° C. cyclic heating and cooling to be suspended by vibration for 24 hours, and then centrifuged to obtain crystal form O of the pamoate of the compound of formula I, which was detected by XRPD. The XRPD pattern obtained is shown in FIG. 15.

Example 16: Preparation of Crystal Form P of the Pamoate of the Compound of Formula I 50 mg of the compound of formula I and 46 mg of pamoic acid were taken into 2 mL of acetonitrile, and placed in an environment of 40-10° C. cyclic heating and cooling to be suspended by vibration for 24 hours, and then centrifuged to obtain crystal form P of the pamoate of the compound of formula I, which was detected by XRPD. The XRPD pattern obtained is shown in FIG. 16.

Example 17: Preparation of Crystal Form Q of the Pamoate of the Compound of Formula I 50 mg of the compound of formula I and 46 mg of pamoic acid were taken into 2 mL of isopropanol, and placed in an environment of 40-10° C. cyclic heating and cooling to be suspended by vibration for 24 hours, and then centrifuged to obtain crystal form Q of the pamoate of the compound of formula I, which was detected by XRPD. The XRPD pattern obtained is shown in FIG. 17.

Example 18: Preparation of Crystal Form R of the Pamoate of the Compound of Formula I 50 mg of the compound of formula I and 46 mg of pamoic acid were taken into 2 mL of THF, and placed in an environment of 40-10° C. cyclic heating and cooling to be suspended by vibration for 24 hours, and then centrifuged to obtain crystal form R of the pamoate of the compound of formula I, which was detected by XRPD. The XRPD pattern obtained is shown in FIG. 18.

Example 19: Preparation of Crystal Form S of the Pamoate of the Compound of Formula I 50 mg of the compound of formula I and 46 mg of pamoic acid were taken into a mixed solvent of 0.4 mL of ethanol and 1.6 mL of n-heptane, and placed in an environment of 40-10° C. cyclic heating and cooling to be suspended by vibration for 24 hours, and then centrifuged to obtain crystal form S of the pamoate of the compound of formula I, which was detected by XRPD. The XRPD pattern obtained is shown in FIG. 19.

Example 20: Preparation of Crystal Form T of the Palmitate of the Compound of Formula I 2.0 g of the compound of formula I and 2.4 g of palmitic acid were taken into 30 mL of ethyl acetate, and stirred at 25° C. for 2 hours, and then filtered to obtain crystal form T of the palmitate of the compound of formula I, which was detected by XRPD. The XRPD pattern obtained is shown in FIG. 20.

Example 21: Preparation of Crystal Form U of the Palmitate of the Compound of Formula I 20 mg of crystal form T of the palmitate of the compound of formula I (obtained from the preparation of Example 20) was taken into 1 mL of ethanol, and placed in an environment of 40-10° C. cyclic heating and cooling to be suspended by vibration for 24 hours, and then centrifuged to obtain crystal U of the palmitate of the compound of formula I, which was detected by XRPD. The XRPD pattern obtained is shown in FIG. 21.

Example 22: Preparation of Crystal Form V of the Palmitate of the Compound of Formula I 20 mg of crystal form T of the palmitate of the compound of formula I (obtained from the preparation of Example 20) was taken into 1 mL of acetone, and placed in an environment of 40-10° C. cyclic heating and cooling to be suspended by vibration for 24 hours, and then centrifuged to obtain crystal form V of the palmitate of the compound of formula I, which was detected by XRPD. The XRPD pattern obtained is shown in FIG. 22.

Experimental Example 1: Solubility Test 1-1 Solubility of Crystal Form T, Crystal Form U, Crystal Form V and the Compound of Formula I The samples were taken into pure water, and an excess amount of samples were added, which were then shaked at room temperature for 15 h, and filtered, and detected by HPLC. HPLC test conditions: mobile phase: sodium octanesulfonate-potassium dihydrogen phosphate buffer solution (5.0 g of sodium octanesulfonate and 9.1 g of potassium dihydrogen phosphate were taken, and added into 1000 ml of water for dissolution, and the pH was adjusted to 3.0 with phosphoric acid)-acetonitrile (72:28); The detection wavelength was 264 nm; The flow rate was 1.5 ml per minute; The column temperature was 40° C.; Injection volume: 10 μl; Chromatographic column: octadecyl silane bonded silica gel as filler (CAPCELL PAK MG II C18, 4.6 mm×250 mm, 5 μm).

| Crystal Forms | Crystal form T | Crystal form U | Crystal form V | Compound of formula I |
|---|---|---|---|---|
| Solubility (mg/ml) | 0.010 | 0.017 | 0.016 | 0.14 |

It can be seen from the data in the above table that compared with the free base of the compound of formula I, the crystals of present disclosure have lower solubility, and can be used for long-acting sustained release formulations.

1-2 Solubility of Crystal Form D and Crystal Form N

The crystal form D and crystal form N of the pamoate were tested by the test method of 1-1. The solubility test results are shown in the following table.

| Name | Solubility (mg/ml) |
|---|---|
| Crystal form D | 0.018 |
| Crystal form N | 0.046 |
| Compound of formula I | 0.14 |

It can be seen from the data in the above table that compared with the free base of the compound of formula I, the crystals of present disclosure have lower solubility, and can be used for long-acting sustained release formulations.

Experimental Example 2 Pharmacokinetic Test in Rats 2-1 Pharmacokinetic Test of Pamoate in Rats 4 female rats were administered with 5 mg/kg of crystal form D of the pamoate of the compound of formula I by intramuscular injection only once. Prior to and 5 min, 15 min, 30 min, 1 h, 2 h, 4 h, 8 h, 24 h, 48 h, 72 h, 96 h, 120 h, 144 h, 168 h after administration, 0.3 ml of venous blood samples (EDTA-K2 anticoagulation) were taken respectively. Then the blood concentration after administration was measured and the concentration-time curve was fitted to calculate the pharmacokinetic parameters. Relevant data are provided in the table below.

| Pharmacokinetic data of pamoate crystals | |
|---|---|
| PK parameters | Value |
| $T_{1/2}$ (h) | 4.88 |
| $T_{max}$ (h) | 0.625 |
| $C_{max}$ (ng/ml) | 389 |
| $AUC_{last}$ (h*ng/ml) | 1624 |
| $AUC_{INF}$ (h*ng/ml) | 1639 |
| Vz_F (ml) | 55549 |
| Cl_F (ml/h) | 7519 |
| $MRT_{last}$ (h) | 4.11 |

According to FDA data (FDA Mirapex® ER™ (pramipexole dihydrochloride), NDA 22-421, Serial 000 received 10/24/08), it can be seen that after administration of the compound of formula I (Pramipexole) to rats, the obtained $T_{max}$ was 0.5 h and $T_{1/2}$ was 3.18 h. It can be seen that, compared with the compound of formula I per se, the crystal form of the pamoate of compound of formula I of present disclosure can maintain the effective blood concentration for a longer time, and had a longer $T_{max}$ and $T_{1/2}$ time, which achieved the effect of long-acting sustained release.

2-2 Pharmacokinetics Test of Palmitate in Rats 4 female rats were administered with 5 mg/kg of crystal form T of the palmitate of the compound of formula I by intramuscular injection only once. Prior to and 5 min, 15 min, 30 min, 1 h, 2 h, 4 h, 8 h, 24 h, 48 h, 72 h, 96 h, 120 h, 144 h, 168 h after administration, 0.3 ml of venous blood samples (EDTA-K2 anticoagulation) were taken respectively. Then the blood concentration after administration was measured and the concentration-time curve was fitted to calculate the pharmacokinetic parameters. Relevant data are provided in the table below.

| Pharmacokinetic data of palmitate | |
|---|---|
| PK parameters | Value |
| $T_{1/2}$ (h) | 21.0 |
| $T_{max}$ (h) | 1.33 |
| $C_{max}$ (ng/ml) | 949 |
| $AUC_{last}$ (h*ng/ml) | 10116 |
| $AUC_{INF}$ (h*ng/ml) | 10205 |
| Vz_F (ml) | 15091 |
| Cl_F (ml/h) | 521 |
| $MRT_{last}$ (h) | 22.3 |

According to FDA data (FDA Mirapex® ER™ (pramipexole dihydrochloride), NDA 22-421, Serial 000 received 10/24/08), it can be seen that after administration of the compound of formula I (Pramipexole) to rats, the obtained $T_{max}$ was 0.5 h and $T_{1/2}$ was 3.18 h. It can be seen that, compared with the compound of formula I per se, the crystal form of the palmitate of the compound of formula I of present disclosure can maintain the effective blood concentration for a longer time, and had a longer $T_{max}$ and $T_{1/2}$ time, which achieved the effect of long-acting sustained release.

The above specific embodiments further describe present disclosure in details. However, it should not be understood that the scope of present disclosure is limited to the listed embodiments, and all technical solutions based on the contents of present disclosure fall within the scope of present disclosure.

The invention claimed is:

1. A palmitate salt of a compound of formula I,

I

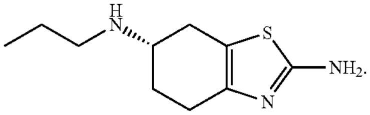

2. The palmitate salt of the compound of formula I according to claim 1, wherein the stoichiometric ratio of the compound of formula I to palmitic acid is 1:1.

3. A crystal form of the palmitate salt of the compound of formula I according to claim 2,

I

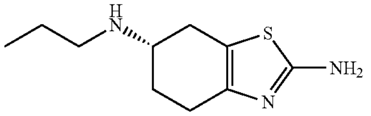

which is selected from the group consisting of:

(1) Crystal form T, wherein the crystal form T has an XRPD pattern comprising diffraction peaks at 2θ of about 6.17±0.2°, 9.73±0.2°, 10.20±0.2°, 11.52±0.2°, 12.44±0.2°, 15.16±0.2° and 21.40±0.2°;

(2) Crystal U, wherein the crystal form U has an XRPD pattern comprising diffraction peaks at 2θ of about 5.95±0.2°, 15.15±0.2°, 17.90±0.2°, 20.57±0.2°, 21.44±0.2°, 21.83±0.2° and 25.82±0.2°; and (3) Crystal V, wherein the crystal form V has an XRPD pattern comprising diffraction peaks at 2θ of about 5.56±0.2°, 12.99±0.2°, 13.21±0.2°, 13.59±0.2°, 14.02±0.2°, 14.71±0.2° and 19.90±0.2°.

4. A pharmaceutical composition, comprising:

i) the palmitate salt of the compound of formula I according to claim 1;

ii) one or more pharmaceutically acceptable carriers.

5. A method for treating Parkinson's disease and restless leg syndrome, comprising administering the palmitate salt of the compound of formula I according to claim 1 to a subject in need thereof.

6. The crystal form of the palmitate salt of the compound of formula I according to claim 3, being crystal form T, wherein the XRPD pattern of crystal form T further comprises diffraction peaks at 2θ of about 13.82±0.2°, 16.36±0.2° and 16.65±0.2°.

7. The crystal form of the palmitate salt of the compound of formula I according to claim 6, being crystal form T, wherein the XRPD pattern of crystal form T further comprises diffraction peaks at 2θ of about 16.89±0.2°, 19.88±0.2° and 20.18±0.2°.

8. The crystal form of the palmitate salt of the compound of formula I according to claim 3, being crystal form T, wherein the crystal form T of the palmitate salt of the compound of formula I has an XRPD pattern substantially as shown in FIG. 20.

9. A pharmaceutical composition, comprising:

i) the palmitate salt of the compound of formula I according to claim 2;

ii) one or more pharmaceutically acceptable carriers.

10. A pharmaceutical composition, comprising:

i) the crystal form of the palmitate salt of the compound of formula I according to claim 3;

ii) one or more pharmaceutically acceptable carriers.

11. A pharmaceutical composition, comprising:

i) the crystal form of the palmitate salt of the compound of formula I according to claim 6;

ii) one or more pharmaceutically acceptable carriers.

12. A pharmaceutical composition, comprising:

i) the crystal form of the palmitate salt of the compound of formula I according to claim 7;

ii) one or more pharmaceutically acceptable carriers.

13. A pharmaceutical composition, comprising:

i) the crystal form of the palmitate salt of the compound of formula I according to claim 8;

ii) one or more pharmaceutically acceptable carriers.

14. A method for treating Parkinson's disease and restless leg syndrome, comprising administering the palmitate salt of the compound of formula I according to claim 2 to a subject in need thereof.

15. A method for treating Parkinson's disease and restless leg syndrome, comprising administering the crystal form of the palmitate salt of the compound of formula I according to claim 3 to a subject in need thereof.

16. A method for treating Parkinson's disease and restless leg syndrome, comprising administering the pharmaceutical composition according to claim 4 to a subject in need thereof.

17. The crystal form of the palmitate salt of the compound of formula I according to claim 3, being crystal form U, wherein the XRPD pattern further comprises diffraction peaks at 2θ of about 10.81±0.2°, 14.47±0.2°, 18.20±0.2°, 22.63±0.2° and 26.63±0.2°.

18. The crystal form of the palmitate salt of the compound of formula I according to claim 17, being crystal form U, wherein the XRPD pattern further comprises diffraction peaks at 2θ of about 11.27±0.2° and 26.03±0.2°.

19. The crystal form of the palmitate salt of the compound of formula I according to claim 3, being crystal form U, wherein the crystal form U of the palmitate salt of the compound of formula I has an XRPD pattern substantially as shown in FIG. 21.

20. The crystal form of the palmitate salt of the compound of formula I according to claim 3, being crystal form V, wherein the XRPD pattern further comprises diffraction peaks at 2θ of about 11.19±0.2°, 19.66±0.2°, 22.61±0.2°, 22.80±0.2° and 23.43±0.2°.

21. The crystal form of the palmitate salt of the compound of formula I according to claim 20, being crystal form V, wherein the XRPD pattern further comprises diffraction peaks at 2θ of about 11.38±0.2°, 19.48±0.2°, 20.26±0.2° and 22.96±0.2°.

22. The crystal form of the palmitate salt of the compound of formula I according to claim 3, being crystal form V, wherein the crystal form V of the palmitate salt of the compound of formula I has an XRPD pattern substantially as shown in FIG. 22.

23. A pharmaceutical composition, comprising:

i) the crystal form of the palmitate salt of the compound of formula I according to claim 17;

ii) one or more pharmaceutically acceptable carriers.

24. A pharmaceutical composition, comprising:

i) the crystal form of the palmitate salt of the compound of formula I according to claim 18;

ii) one or more pharmaceutically acceptable carriers.

25. A pharmaceutical composition, comprising:

i) the crystal form of the palmitate salt of the compound of formula I according to claim 19;

ii) one or more pharmaceutically acceptable carriers.

26. A pharmaceutical composition, comprising:

i) the crystal form of the palmitate salt of the compound of formula I according to claim 20;

ii) one or more pharmaceutically acceptable carriers.

27. A pharmaceutical composition, comprising:

i) the crystal form of the palmitate salt of the compound of formula I according to claim 21;

ii) one or more pharmaceutically acceptable carriers.

28. A pharmaceutical composition, comprising:

i) the crystal form of the palmitate salt of the compound of formula I according to claim 22;

ii) one or more pharmaceutically acceptable carriers.

* * * * *